US009518995B2

(12) United States Patent
Baulieu et al.

(10) Patent No.: US 9,518,995 B2
(45) Date of Patent: Dec. 13, 2016

(54) FKBP52-TAU INTERACTION AS A NOVEL THERAPEUTICAL TARGET FOR TREATING THE NEUROLOGICAL DISORDERS INVOLVING TAU DYSFUNCTION

(71) Applicant: Institut National de la Sante et de la Recherche Medicale (INSERM), Paris (FR)

(72) Inventors: Etienne Baulieu, Le Kremlin Bicetre (FR); Beatrice Chambraud, Le Kremlin Bicetre (FR)

(73) Assignee: Institut National de la Sante et de la Recherche Medicale (INSERM), Paris (FR)

( * ) Notice: Subject to any disclaimer, the term of this patent is extended or adjusted under 35 U.S.C. 154(b) by 0 days.

(21) Appl. No.: 14/814,674

(22) Filed: Jul. 31, 2015

(65) Prior Publication Data

US 2016/0047823 A1 Feb. 18, 2016

Related U.S. Application Data

(63) Continuation of application No. 14/132,832, filed on Dec. 18, 2013, now Pat. No. 9,128,104, which is a continuation of application No. 13/497,907, filed as application No. PCT/EP2010/064115 on Sep. 24, 2010, now Pat. No. 8,648,044.

(30) Foreign Application Priority Data

Sep. 24, 2009 (EP) .................................... 09305893
Jan. 22, 2010 (EP) .................................... 10305074

(51) Int. Cl.
*G01N 33/68* (2006.01)

(52) U.S. Cl.
CPC ... *G01N 33/6896* (2013.01); *G01N 2333/4709* (2013.01); *G01N 2500/00* (2013.01); *G01N 2500/02* (2013.01); *G01N 2800/28* (2013.01); *G01N 2800/2821* (2013.01); *G01N 2800/2828* (2013.01); *G01N 2800/2835* (2013.01)

(58) Field of Classification Search
None
See application file for complete search history.

(56) References Cited

U.S. PATENT DOCUMENTS

2003/0194742 A1 10/2003 Vanmechelen et al.
2009/0162336 A1 6/2009 Mandelkow et al.

FOREIGN PATENT DOCUMENTS

WO 2005/109004 11/2005

OTHER PUBLICATIONS

Goris 2007 "tau and alpha synuclein in susceptibility to, and dementia in, parkinson's disease" ann neurol 62(2):145-53.*
Kraemer 2006 "molecular pathways that influence human tau-induced pathology in caenorhabditis elegans" Human molecular genetics 15(9):1483-1496.*
Tatro 2009 "Differential expression of immunophillins fkbp51 and fkbp52 in the frontal cortex of hiv-infected patients with major depressive disorder" J neuroimmune pharmacol 4(2):218-226.*
Rafii and Aisen, "Recent developments in Alzheimer's disease therapeutics", BMC, 2009, pp. 1-4, vol. 7, No. 7.
Kraemer et al., "Molecular pathways that influence human tau-induced pathology in Caenorhabditis elegans", Human Mol Gen, 2006, pp. 1483-1496, vol. 15, No. 9.
Tortosa et al., "Binding of Hsp90 to tau promotes a conformational change and aggregation of tau protein", JAD, 2009, pp. 319-325, vol. 17.
Chun and Johnson, "Activation of Glycogen synthase kinase 3beta promotes the intermolecular association of tau: the use of fluorescence resonance energy transfer microscopy", JBC, 2007, pp. 23410-23417, vol. 282.
Chambraud et al., "The immunophilin FKBP52 specifically binds to tubulin and prevents microtubule formation", The FASEB Journal: Official Publication of the Federation of American Societies for Experimental Biologies, Oct. 9, 2008, pp. 206-212.
Davies et al., "FKBP52", The International Journal of Biochemistry and Cell Biology, Jan. 2005, pp. 42-47, vol. 37, No. 1.
Avramut, "immunophilins and their ligands: insights into survival and growth of human neurons", Phys Behav, 2002, pp. 463-468, vol. 77.
"FKBP4", 2015, NCBI-2288, Web.

* cited by examiner

*Primary Examiner* — Adam M Weidner
(74) *Attorney, Agent, or Firm* — Whitham, Curtis & Cook, P.C.

(57) ABSTRACT

Candidate compounds for use in neuro-protection and repair in neurological disorders involving Tau dysfunction (including Alzheimer's disease) are identified from a direct interaction between proteins FKBP52 and Tau. The method for screening a drug for the prevention and treatment of neurological disorders involving Tau dysfunction includes determining the ability of a candidate compound, to modulate binding between a Tau polypeptide and a FKBP52 polypeptide, and selecting positively the candidate compound that modulates binding.

5 Claims, 12 Drawing Sheets

Figure 1:
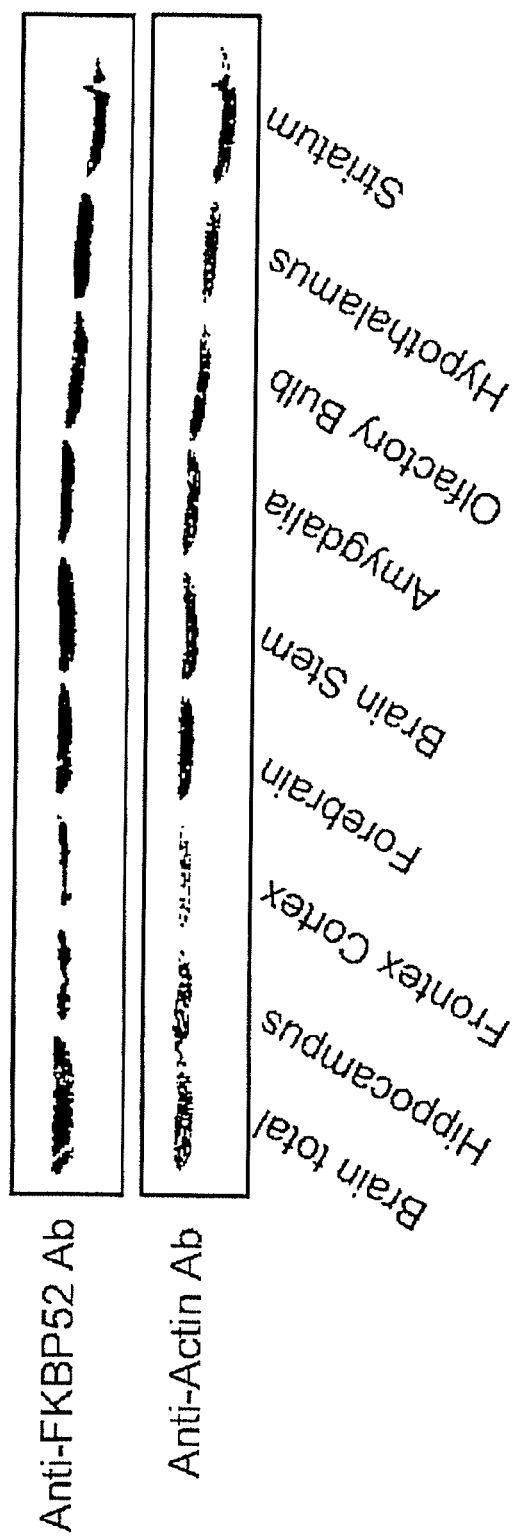

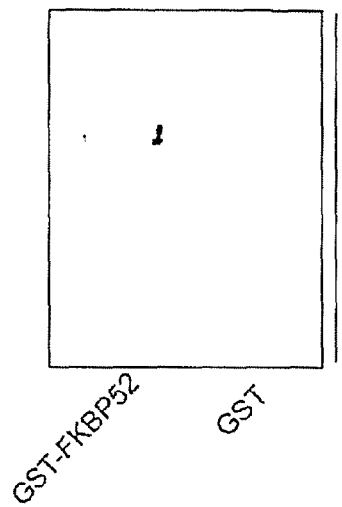
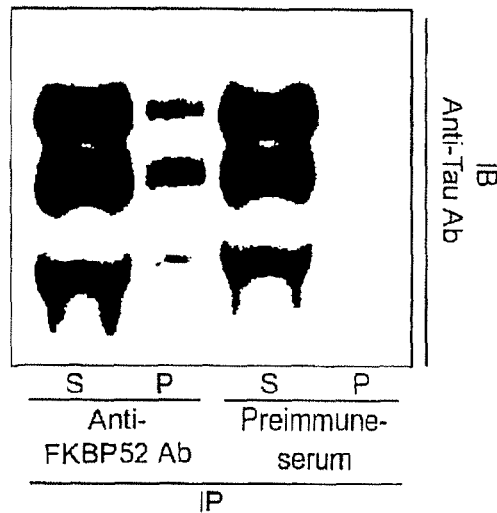
Fig. 2A
Fig. 2B
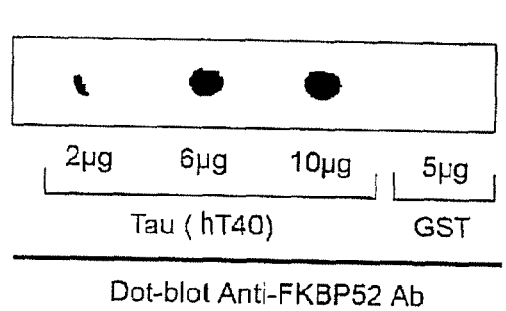
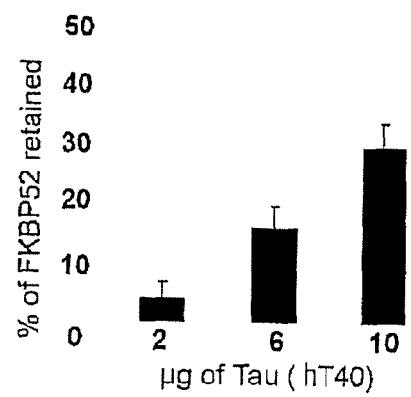
Fig. 2C
Fig. 2D

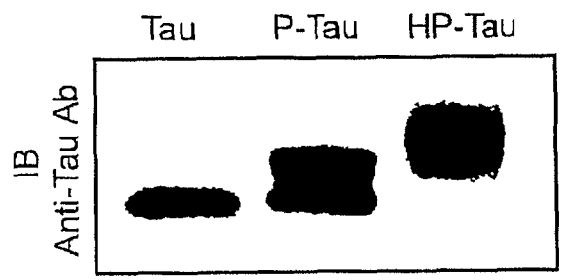
Fig. 3A
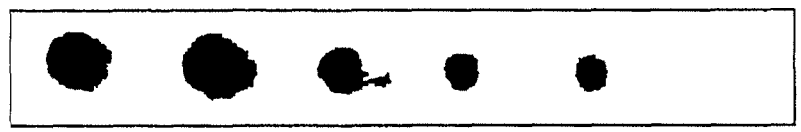
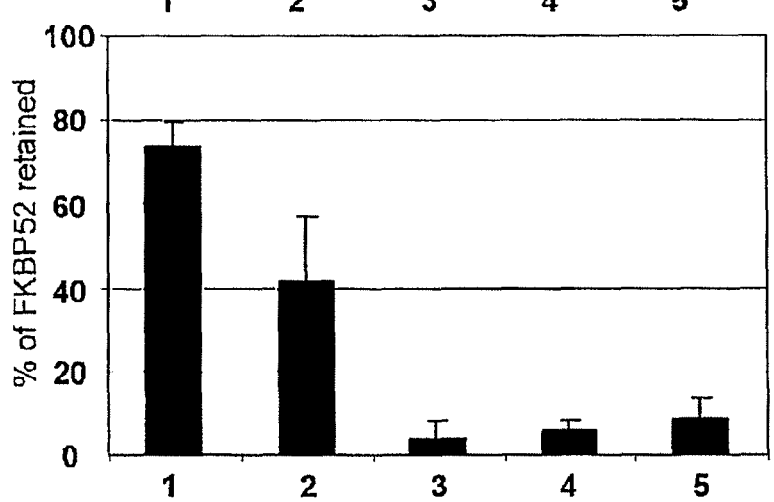
Fig. 3B
Fig. 3C

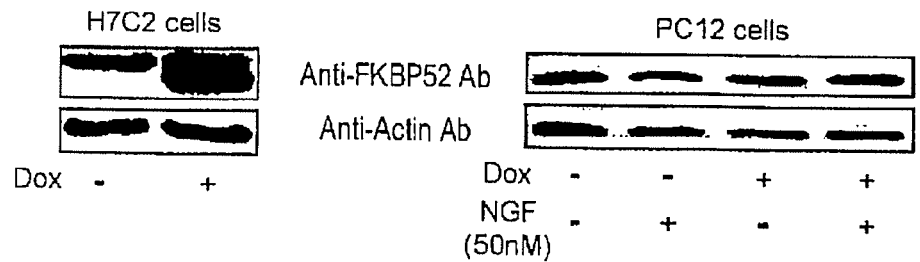
Fig. 6B          Fig. 6A
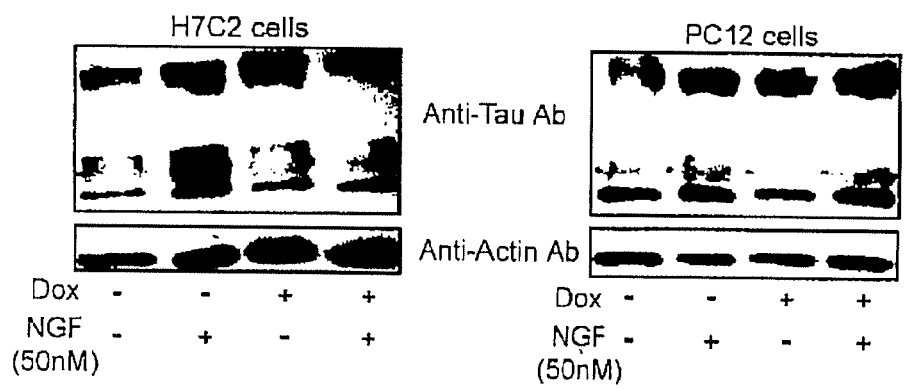
Fig. 6C          Fig. 6D
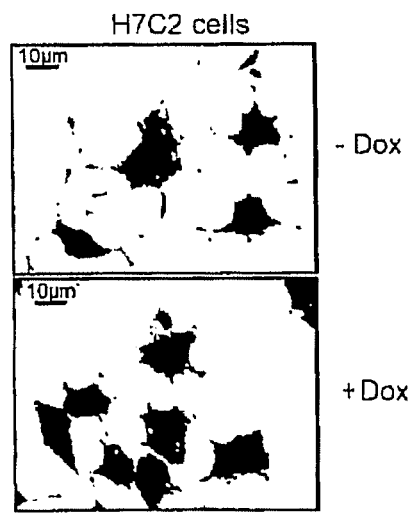
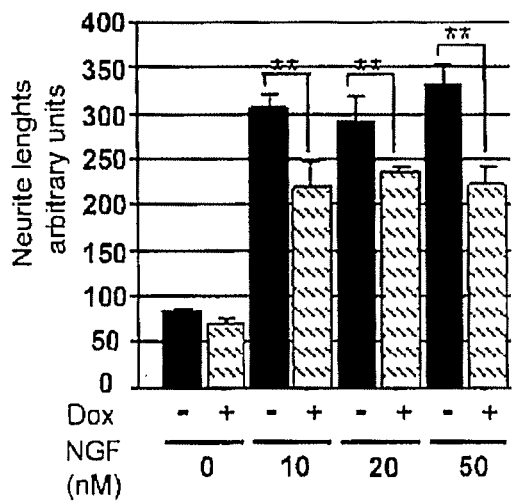
Fig. 6E          Fig. 6F Fig. 7A
Fig. 7B
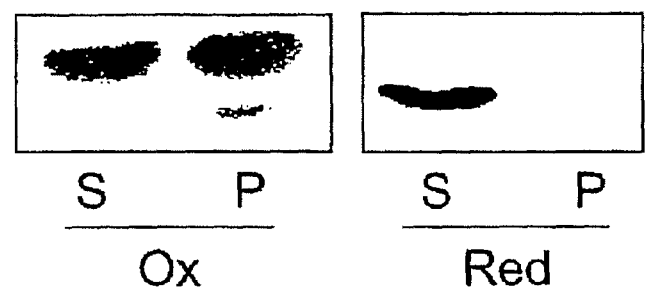
S   P
Ox
S   P
Red
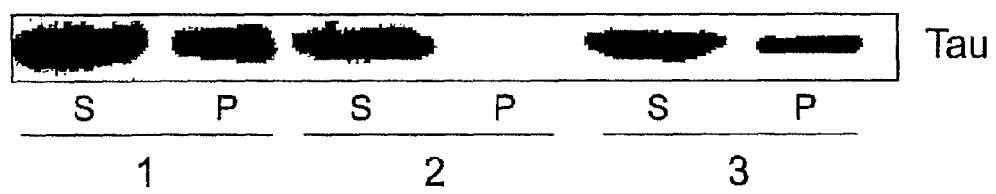
Tau
S   P   S   P   S   P
  1       2       3
Fig. 8

FKBP52-TAU INTERACTION AS A NOVEL THERAPEUTICAL TARGET FOR TREATING THE NEUROLOGICAL DISORDERS INVOLVING TAU DYSFUNCTION

CROSS-REFERENCE TO RELATED APPLICATIONS

The present application is a continuation application of U.S. Utility application Ser. No. 14/132,832, filed Dec. 18, 2012, which is a continuation application of U.S. Utility application Ser. No. 13/497,907, filed Aug. 9, 2012, which is a 371 of International Application PCT/EP2010/064115, filed Sep. 24, 2010, which claims priority to European Application 09305893.1, filed Sep. 24, 2009, and European Application 10305074.6, filed Jan. 22, 2010.

FIELD OF THE INVENTION

The invention relates generally to neuroprotection and repair in neurological disorders involving Tau dysfunction (including Alzheimer's disease). The invention describes a direct interaction between proteins FKBP52 and Tau. The invention relates to a screening method for molecules acting on FKBP52-Tau interaction, in order to modulate the detrimental effects of pathogenic Tau. The present invention finally relates to therapeutical diagnostic, prognostic, and monitoring assays of neurological disorders involving Tau dysfunction.

BACKGROUND OF THE INVENTION

The Tau protein is a major Microtubule Associated Protein (MAP) widely expressed in the central nervous system, predominantly in neurons, where it plays a key role in regulating microtubule dynamics, axonal transport and neurite outgrowth. Protein Tau occurs in the adult human brain under six different isoforms generated by alternative splicing of exons 2, 3 and 10 of a primary transcript of a unique gene located on chromosome 17. The length of their sequences varies from 352 to 441 amino acids. Growing evidence suggests that aberrant assembly of "aggregated" Tau (natively unfolded protein) is a hallmark of a series of human cognitive diseases collectively referred to as tauopathies or neurological disorders involving Tau dysfunction, which include Alzheimer's disease, Pick's disease, corticobasal degeneration, mild cognitive impairment, progressive supranuclear palsy, and frontotemporal dementia with chromosome 17-linked parkinsonism. Abnormalities of Tau such as hyperphosphorylation, mutation, truncation and the aggregation in "tangles" may be contributing factors to the pathogenic processes. To date the role of Tau modifications in the induction of neurodegenerative diseases is not fully understood and deciphering the molecular mechanism(s) which control(s) Tau structure/function is therefore of great interest and may help to find novel therapeutic approaches for these diseases.

The instant invention is based on the discovery that Tau protein (all 6 isoforms) binds specifically and directly the immunophilin FKBP52 (FK506-Binding Protein). FKBPs are a family of ubiquitously expressed intracellular receptors for the powerful immunosuppressant drugs FK506 and Rapamycin and therefore take place in the large group of proteins known as immunophilins. These proteins show a large distribution and are particularly abundant in the nervous system suggesting novel and unexpected functions distinct from their immunomodulatory effects. In addition, neuroprotective effects of FK506 have been reported. These latter observations have provided new perspectives for the FKBP protein family and a particular interest for FK506 and its non immunosuppressive derivative molecules as factors to devise new therapeutic assay for treating lesions and diseases of the nervous system.

FKBP52, first identified and cloned as associated to steroid receptor (Lebeau et al., 1992), presents a modular organization. Including four individual and functional domains (Callebaut et al., 1992). The FK506 binding site of FKBP52 (domain I) localized in the N-terminal part of the protein (aa 1 to 149) contains a peptidyl prolyl-isomerase (PPIase) activity (Chambraud et al., 1993) characteristic of all immunophilin protein family. While the second domain (aa 149 to 267) shares structural homology with domain I, the PPIase activity is residual and it does not bind FK506 (14,15); a noteworthy aspect of domain II is a consensus ATP-GTP-binding sequence (16). The C-terminal domain, covering domains III and IV, includes a putative calmodulin binding site (Massol et al., 1992) and mediates, through its three tetratricopeptide repeat (TPR) (aa 273 to 389) the protein's interaction with HSP90 (Radanyi et al., 1994) which is also a component of steroid receptor complex (Catelli et al., 1980, Tai et al., 1986; Renoir et al., 1990). In addition the binding activity of FKBP52 with HSP90 is regulated by casein kinase II which specifically phosphorylates FKBP52 (Myata et al., 1997).

Recently it has been reported that FKBP52 interacts with microtubules and prevents tubulin polymerization (Chambraud et al., 2007). Results obtained so far suggest that this inhibition of tubulin polymerization by FKBP52 may not only result from the sequestration of tubulin or from a modification of its structure, such a bending, by FKBP52, but that another important factor required in the assembling of tubulin into microtubules may be involved.

The inventors now postulate herein that the intervention of one or more microtubule stabilizing factor(s), such as microtubule-associated proteins (MAPs), could explain the inhibition of tubulin polymerization by FKBP52. Using classical biochemical and cellular approaches they establish solid foundations to the role of FKBP52 on Tau function and discover a direct and specific interaction between FKBP52 and Tau. This FKBP52-Tau interaction results in the modulation of the known Tau-mediated cellular functions such as: tubulin polymerization (FKBP52 inhibits this function), Tau accumulation (FKBP52 inhibits this accumulation) and neurite outgrowth.

SUMMARY OF THE INVENTION

The inventors have discovered a direct and specific protein-protein interaction between the immunophilin FKBP52 and the microtubule associated protein Tau (under all of its known isoforms, hyperphosphorylated or not). The invention establishes that the FKBP52-Tau interaction provides a new target that may be used advantageously for novel therapeutic approaches of neurological disorders involving Tau dysfunction, and especially for Alzheimer's disease.

Therefore invention provides methods for identifying molecules that modulate the FKBP52-Tau interaction, therefore acting beneficially onto the detrimental effects of the neurological disorders involving Tau dysfunction.

The molecules identified via the method of the invention for their ability to modulate the interaction between Tau and FKBP52 are drug candidates for the prevention and treatment of neurological disorders involving Tau dysfunction and in particular for the Alzheimer's disease.

The invention also establishes that the FKBP52-Tau interaction provides a biological marker, potentially involved in diagnostic, prognostic, clinical follow-ups.

DETAILED DESCRIPTION OF THE INVENTION

Screening Methods of the Invention

A first object of the invention consists of a method for screening a drug for the prevention and treatment of neurological disorders involving Tau dysfunction comprising the following steps:

a) determining the ability of a candidate compound to modulate the interaction between a Tau polypeptide and a FKBP52 polypeptide and b) selecting positively the candidate compound that modulates said interaction.

As used herein the term "neurological disorders involving Tau dysfunction" includes but is not limited to Alzheimer's disease, frontotemporal dementia, progressive supranuclear palsy, corticobasal degeneration and frontotemporal lobar degeneration, also known as Pick's disease, as well as all neurological disorders which might, in the future, prove to involve Tau, such as the Parkinson disease for instance.

In the context of the invention, the term "treating" or "treatment", as used herein, means reversing, alleviating, or inhibiting the progress of the disorder or condition to which such term applies, or one or more symptoms of such disorder or condition.

As used herein, the term "prevention" refers to preventing the disease or condition from occurring in a subject which has not yet been diagnosed as having it.

As used herein the expression "a compound that modulates the interaction between FKBP52 and Tau" refers any compound having the capability to inhibit, decrease or enhance the interaction between protein Tau and protein FKBP52.

At step a), any method suitable for the screening of protein-protein interactions is suitable.

Whatever the embodiment of step a) of the screening method, the complete Tau protein and the complete FKBP52 protein may be used as the binding partners. Alternatively, fragments of Tau protein and FKBP52 protein that include the site of interaction may be uses as the binding partners.

Therefore in one embodiment step a) of the screening method of the invention consists of the following steps:

a1) bringing into contact the candidate compound to be tested with a mixture of a first Tau polypeptide or a substantially homologous or substantially similar amino acid sequence thereof and (2) a second FKBP52 polypeptide or a substantially homologous or substantially similar amino acid sequence thereof a2) determining the ability of said candidate compound to modulate the binding between said Tau polypeptide and said second FKBP52 polypeptide.

The term "polypeptide" means herein a polymer of amino acids having no specific length. Thus, peptides, oligopeptides and proteins are included in the definition of "polypeptide" and these terms are used interchangeably throughout the specification, as well as in the claims. The term "polypeptide" does not exclude post-translational modifications that include but are not limited to phosphorylation, acetylation, glycosylation. and the like. Especially, the term includes all phosphoryaled forms of the polypeptide (e.g. all phosphorylated forms of Tau or FKBP52). Also encompassed by this definition of "polypeptide" are homologs thereof.

Accordingly, the term "Tau polypeptide" refers to the Tau protein or a fragment thereof that comprises the site of interaction with FKBP52 protein. In the same manner, the term "FKBP52 polypeptide" refers to the FKBP52 protein or a fragment thereof that comprises the site of interaction with Tau protein.

Two amino acid sequences are "substantially homologous" or "substantially similar" when greater than 80%, preferably greater than 85%, preferably greater than 90% of the amino acids are identical, or greater than about 90%, preferably grater than 95° A), are similar (functionally identical). The term "sequence identity" refers to the identity between two peptides. Identity between sequences can be determined by comparing a position in each of the sequences which may be aligned for the purposes of comparison. When a position in the compared sequences is occupied by the same base or amino acid, then the sequences are identical at that position. A degree of sequence identity between nucleic acid sequences is a function of the number of identical nucleotides at positions shared by these sequences. A degree of identity between amino acid sequences is a function of the number of identical amino acid sequences that are shared between these sequences. To determine the percent identity of two amino acids sequences or two nucleic acid sequences, the sequences are aligned for optimal comparison. For example, gaps can be introduced in the sequence of a first amino add sequence or a first nucleic acid sequence for optimal alignment with the second amino acid sequence or second nucleic acid sequence. The amino acid residues or nucleotides at corresponding amino acid positions or nucleotide positions are then compared. When a position in the first sequence is occupied by the same amino acid residue or nucleotide as the corresponding position in the second sequence, the molecules are identical at that position. The percent identity between the two sequences is a function of the number of identical positions shared by the sequences. In this comparison the sequences can be the same length or may be different in length. Optimal alignment of sequences for determining a comparison window may be conducted by the local homology algorithm of Smith and Waterman (J. Theor. Biol., 91 (2) pgs. 370-380 (1981), by the homology alignment algorithm of Needleman and Wunsch, J. Miol. Biol., 48 (3) pgs. 443-453 (1972), by the search for similarity via the method of Pearson and Lipman, PNAS, USA, 85 (5) pgs. 2444-2448 (1988), by computerized implementations of these algorithms (GAP, BESTFIT, FASTA and TFASTA in the Wisconsin Genetics Software Package Release 7.0, Genetic Computer Group, 575, Science Drive, Madison, Wis.) or by inspection. The term "sequence similarity" means that amino acids can be modified while retaining the same function. It is known that amino acids are classified according to the nature of their side groups and some amino adds such as the basic amino acids can be interchanged for one another while their basic function is maintained.

In one embodiment the step a2) consists in generating physical values which illustrate or not the ability of said candidate compound to modulate the interaction between said first polypeptide and said second polypeptide and comparing said values with standard physical values obtained in the same assay performed in the absence of the said candidate compound. The "physical values" that are referred to above may be of various kinds depending of the binding assay that is performed, but notably encompass light absorbance values, radioactive signals and intensity value of fluorescence signal. If after the comparison of the physical values with the standard physical values, it is determined that the said candidate compound modulates the binding between said first polypeptide and said second polypeptide, then the candidate is positively selected at step b).

The compounds that modulate the interaction between (i) the Tau polypeptide and (ii) the FKBP52 polypeptide encompass those compounds that bind either to the Tau polypeptide or to FKBP52 polypeptide, provided that the binding of the said compounds of interest then modulates the interaction between Tau and FKBP52.

Polypeptides of the invention may be produced by any technique known per se in the art, such as without limitation, any chemical, biological, genetic or enzymatic technique, either alone or in combination(s).

Knowing the amino acid sequence of the desired sequence, one skilled in the art can readily produce said polypeptides, by standard techniques for production of polypeptides. For instance, they can be synthesized using well-known solid phase method, preferably using a commercially available peptide synthesis apparatus (such as that made by Applied Biosystems, Foster City, Calif.) and following the manufacturer's instructions.

Alternatively, the polypeptides of the invention can be synthesized by recombinant DNA techniques as is now well-known in the art. For example, these fragments can be obtained as DNA expression products after incorporation of DNA sequences encoding the desired (poly)peptide into expression vectors and introduction of such vectors into suitable eukaryotic or prokaryotic hosts that will express the desired polypeptide, from which they can be later isolated using well-known techniques.

A wide variety of host/expression vector combinations are employed in expressing the nucleic acids encoding for the polypeptides of the present invention. Useful expression vectors that can be used include, for example, segments of chromosomal, non-chromosomal and synthetic DNA sequences. Suitable vectors include, but are not limited to, derivatives of SV40 and pcDNA and known bacterial plasmids such as col EI, pCR1, pBR322, pMal-C2, pET, pGEX, pMB9 and derivatives thereof, plasmids such as RP4, phage DNAs such as the numerous derivatives of phage I such as NM989, as well as other phage DNA such as M13 and filamentous single stranded phage DNA; yeast plasmids such as the 2 microns plasmid or derivatives of the 2 microns plasmid, as well as centomeric and integrative yeast shuttle vectors; vectors useful in eukaryotic cells such as vectors useful in insect or mammalian cells; vectors derived from combinations of plasmids and phage DNAs, such as plasmids that have been modified to employ phage DNA or the expression control sequences; and the like.

Consequently, mammalian and typically human cells, as well as bacterial, yeast, fungi, insect, nematode and plant cells an used in the present invention and may be transfected by the nucleic acid or recombinant vector as defined herein. Examples of suitable cells include, but are not limited to, VERO cells, HELA cells such as ATCC No. CCL2, CHO cell lines such as ATCC No. CCL61, COS cells such as COS-7 cells and ATCC No. CRL 1650 cells, W138, BHK, HepG2, 3T3 such as ATCC No. CRL6361, A549, PC12, K562 cells, 293T cells, Sf9 cells such as ATCC No. CRL1711 and Cv1 cells such as ATCC No. CCL70. Other suitable cells that can be used in the present invention include, but are not limited to, prokaryotic host cells strains such as *Escherichia coli*, (e.g., strain DH5-[alpha]), *Bacillus subtilis, Salmonella typhimurium*, or strains of the genera of *Pseudomonas, Streptomyces* and *Staphylococcus*. Further suitable cells that can be used in the present invention include yeast cells such as those of *Saccharomyces* such as *Saccharomyces cerevisiae*.

In one embodiment, any Tau derived or FKBP52 polypeptide of the invention is labelled with a detectable molecule for the screening purposes.

According to the invention, said detectable molecule may consist of any compound or substance that is detectable by spectroscopic, photochemical, biochemical, immunochemical or chemical means. For example, useful detectable molecules include radioactive substance (including those comprising 32P, 25S, 3H, or 125I), fluorescent dyes (including 5-bromodesosyrudin, fluorescein, acetylaminofluorene or digoxigenin), fluorescent proteins (including GFPs and YFPs), or detectable proteins or peptides (including biotin, polyhistidine tails or other antigen tags like the HA antigen, the FLAG antigen, the c-myc antigen and the DNP antigen).

According to the invention, the detectable molecule is located at, or bound to, an amino acid residue located outside the said amino acid sequence of interest, in order to minimise or prevent any artefact for the binding between said polypeptides or between the candidate compound and or any of said polypeptides.

In another particular embodiment, the polypeptides of the invention are fused with a GST tag (Glutathione S-transferase). In this embodiment, the GST moiety of the said fusion protein may be used as detectable molecule. In the said fusion protein, the GST may be located either at the N-terminal end or at the C-terminal end. The GST detectable molecule may be detected when it is subsequently brought into contact with an anti-GST antibody, including with a labelled anti-GST antibody. Anti-GST antibodies labelled with various detectable molecules are easily commercially available.

In another particular embodiment, the polypeptides of the invention are fused with a poly-histidine tag. Said poly-histidine tag usually comprises at least four consecutive hisitidine residues and generally at least six consecutive histidine residues. Such a polypeptide tag may also comprise up to 20 consecutive histidine residues. Said poly-histidine tag may be located either at the N-terminal end or at the C-terminal end In this embodiment, the poly-histidine tag may be detected when it is subsequently brought into contact with an anti-poly-histidine antibody, including with a labelled anti-poly-histidine antibody. Anti-poly-histidine antibodies labelled with various detectable molecules are easily commercially available.

In a further embodiment, the polypeptides of the invention are fused with a protein moiety consisting of either the DNA binding domain or the activator domain of a transcription factor. Said protein moiety domain of transcription may be located either at the N-terminal end or at the C-terminal end. Such a DNA binding domain may consist of the well-known DNA binding domain of LexA protein originating form *E. Coli*. Moreover said activator domain of a transcription factor may consist of the activator domain of the well-known Gal4 protein originating from yeast.

In one embodiment of the screening method according to the invention, the first Tau polypeptide and second FKBP52 polypeptide as described above, comprise a portion of a transcription factor. In said assay, the binding together of the first and second portions generates a functional transcription factor that binds to a specific regulatory DNA sequence, which in turn induces expression of a reporter DNA sequence, said expression being further detected and/or measured. A positive detection of the expression of said reporter DNA sequence means that an active transcription factor is formed, due to the binding together of said first Tau polypeptide and second FKBP52 polypeptide polypeptide.

Usually, in a two-hybrid assay, the first and second portion of a transcription factor consist respectively of (i) the DNA binding domain of a transcription factor and (ii) the activator domain of a transcription factor. In some embodiments, the DNA binding domain and the activator domain both originate from the same naturally occurring transcription factor. In some embodiments, the DNA binding domain and the activator domain originate from distinct naturally occurring factors, while, when bound together, these two portions form an active transcription factor. The term "portion" when used herein for transcription factor, encompass complete proteins involved in multi protein transcription factors, as well as specific functional protein domains of a complete transcription factor protein.

Therefore in one embodiment of the invention, step a) of the screening method of the invention comprises the following steps:
 (1) providing a host cell expressing:
  a first fusion polypeptide between (i) a Tau polypeptide as define above and (ii) a first protein portion of transcription factor
  a second fusion polypeptide between (i) a FKBP52 polypeptide as defined above and (ii) a second portion of a transcription factor
  said transcription factor being active on DNA target regulatory sequence when the first and second protein portion are bound together and
  said host cell also containing a nucleic acid comprising (i) a regulatory DNA sequence that may be activated by said active transcription factor and (ii) a DNA report sequence that is operatively linked to said regulatory sequence
 (2) bringing said host cell provided at step 1) into contact with a candidate compound to be tested
 (3) determining the expression level of said DNA reporter sequence The expression level of said DNA reporter sequence that is determined at step (3) above is compared with the expression of said DNA reporter sequence when step (2) is omitted. A different expression level of said DNA reporter sequence in the presence of the candidate compound means that the said candidate compound effectively modulates the binding between the Tau polypeptide and the FKBP52 polypeptide and that said candidate compound may be positively selected a step b) of the screening method.

Suitable host cells include, without limitation, prokaryotic cells (such as bacteria) and eukaryotic cells (such as yeast cells, mammalian cells, insect cells, plant cells, etc.). However preferred host cell are yeast cells and more preferably a *Saccharomyces cerevisiae* cell or a *Schizosaccharomyces pombe* cell.

Similar systems of two-hybrid assays are well know in the art and therefore can be used to perform the screening method according to the invention (see. Fields et al. 1989; Vasavada et al. 1991; Fearon et al. 1992; Dang et al., 1991; Chien et al. 1991, U.S. Pat. Nos. 5,283,173, 5,667,973, 5,468,614, 5,525,490 and 5,637,463). For instance, as described in these documents, the Gal4 activator domain can be used for performing the screening method according to the invention. Gal4 consists of two physically discrete modular domains, one acting as the DNA binding domain, the other one functioning as the transcription-activation domain. The yeast expression system described in the foregoing documents takes advantage of this property. The expression of a Gal1-LacZ reporter gene under the control of a Gal4-activated promoter depends on the reconstitution of Gal4 activity via protein-protein interaction. Colonies containing interacting polypeptides are detected with a chromogenic substrate for β-galactosidase. A compete kit (MATCHMAKER,™) for identifying protein-protein interactions is commercially available from Clontech.

So in one embodiment, a first Tau polypeptide as above defined is fused to the DNA binding domain of Gal4 and the second FKBP52 polypeptide as above defined is fused to the activation domain of Gal4.

The expression of said detectable marker gene may be assessed by quantifying the amount of the corresponding specific mRNA produced. However, usually the detectable marker gene sequence encodes for detectable protein, so that the expression level of the said detectable marker gene is assessed by quantifying the amount of the corresponding protein produced. Techniques for quantifying the amount of mRNA or protein are well known in the art. For example, the detectable marker gene placed under the control of regulatory sequence may consist of the β-galactosidase as above described.

In another one embodiment, step a) comprises a step of subjecting to a gel migration assay the mixture of the first Tau polypeptide and the second FKBP52 polypeptide as above defined, with or without the candidate compound to be tested and then measuring the binding of the said polypeptides altogether by performing a detection of the complexes formed between said polypeptides. The gel migration assay can be carried out as known by the one skilled in the art.

Therefore in one embodiment of the invention, step a) of the screening method of the invention comprises the following steps:
 (1) providing a first Tau polypeptide and a second FKBP52 polypeptide as defined above
 (2) bringing into contact the candidate compound to be tested with said polypeptides
 (3) performing a gel migration assay a suitable migration substrate with said polypeptides and said candidate compound as obtained at step (2)
 (4) detecting and quantifying the complexes formed between said polypeptides on the migration assay as performed at step (3).

The presence or the amount of the complexes formed between the polypeptides are then compared with the results obtained when the assay is performed in the absence of the candidate compound to be tested.

The detection of the complexes formed between the said two polypeptides may be easily performed by staining the migration gel with a suitable dye and then determining the protein bands corresponding to the protein analysed since the complexes formed between the first and the second polypeptides possess a specific apparent molecular weight. Staining of proteins in gels may be done using any well known methods in the art. Suitable gels are well known in the art but it is preferred to use non denaturant gels. In a general manner, western blotting assays are well known in the art and have been widely described (Rybicki et al., 1982; Towbin et al. 1979; Kurien et al. 2006).

In a particular embodiment, the protein bands corresponding to the polypeptides submitted to the gel migration assay can be detected by specific antibodies. It may used both antibodies directed against the Tau polypeptides and antibodies specifically directed against the FKBP52 polypeptides.

In another embodiment, the said two polypeptides are labelled with a detectable antigen as above described. Therefore, the proteins bands can be detected by specific antibodies directed against said detectable antigen. Preferably, the detectable antigen conjugates to the Tau polypeptide is different from the antigen conjugated to the FKBP52 polypeptide. For instance, the first Tau polypeptide can be fused to a GST detectable antigen and the second FKBP52 polypeptide can be fused with the HA antigen. Then the protein complexes formed between the two polypeptides may be quantified and determined with antibodies directed against the GST and HA antigens respectively.

In another embodiment, step a) included the use of an optical biosensor such as described by Edwards et al. (1997) or also by Szabo et al. (1995). This technique allows the detection of interactions between molecules in real time, without the need of labelled molecules. This technique is indeed based on the surface plasmon resonance (SPR) phenomenon. Briefly, a first protein partner is attached to a surface (such as a carboxymethyl dextran matrix). Then the second protein partner is incubated with the previously immobilised first partner, in the presence or absence of the candidate compound to be tested. Then the binding including the binding level, or the absence of binding between said protein partner is detected. For this purpose, a light beam is directed towards the side of the surface area of the substrate that does not contain the sample to be tested and is reflected by said surface. The SPR phenomenon causes a decrease in the intensity of the reflected light with a combination of angle and wavelength. The binding of the first and second protein partner causes a change in the refraction index on the substrate surface, which change is detected as a change in the SPR signal.

In another one embodiment of the invention, the screening method includes the use of affinity chromatography.

Candidate compounds for use in the screening method above can also be selected by any immunoaffinity chromatography technique using any chromatographic substrate onto which (i) the first Tau polypeptide or (ii) the second FKBP52 polypeptide as above defined, has previously been immobilised, according to techniques well known from the one skilled in the art. Briefly, the Tau polypeptide or the FKBP52 polypeptide as above defined may be attached to a column using conventional techniques including chemical coupling to a suitable column matrix such as agarose, Affi Gel®, or other matrices familiar to those of skill in the art. In some embodiment of this method, the affinity column contains chimeric proteins in which the Tau polypeptide or FKBP52 polypeptide as above defined, is fused to glutathion-s-transferase (GST). Then a candidate compound is brought into contact with the chromatographic substrate of the affinity column previously, simultaneously or subsequently to the other polypeptide among the said first and second polypeptide. The after washing, the chromatography substrate is eluted and the collected elution liquid is analysed by detection and/or quantification of the said later applied first or second polypeptide, so as to determine if, and/or to which extent, the candidate compound has modulated the binding between (i) first Tau polypeptide and (ii) the second FKBP52 polypeptide.

In another one embodiment of the screening method according to the invention, the first Tau polypeptide and the second FKBP52 polypeptide as above defined are labelled with a fluorescent molecule or substrate. Therefore, the potential alteration effect of the candidate compound to be tested on the binding between the first Tau polypeptide and the second FKBP52 polypeptide as above defined is determined by fluorescence quantification.

For example, the first Tau polypeptide and the second FKBP52 polypeptide as above defined may be fused with auto-fluorescent polypeptides, as GFP or YFPs as above described. The first Tau polypeptide and the second FKBP52 polypeptide as above defined may also be labelled with fluorescent molecules that are suitable for performing fluorescence detection and/or quantification for the binding between said polypeptides using fluorescence energy transfer (FRET) assay. The first Tau polypeptide and the second FKBP52 polypeptide as above defined may be directly labelled with fluorescent molecules, by covalent chemical linkage with the fluorescent molecule as GFP or YFP. The first Tau polypeptide and the second FKBP52 polypeptide as above defined may also be indirectly labelled with fluorescent molecules, for example, by non covalent linkage between said polypeptides and said fluorescent molecule. Actually, said first Tau polypeptide and second FKBP52 polypeptide as above defined may be fused with a receptor or ligand and said fluorescent molecule may be fused with the corresponding ligand or receptor, so that the fluorescent molecule can non-covalently bind to said first Tau polypeptide and second FKBP52 polypeptide. A suitable receptor/ligand couple may be the biotin/streptavifin paired member or may be selected among an antigen/antibody paired member. For example, a polypeptide according to the invention may be fused to a poly-histidine tail and the fluorescent molecule may be fused with an antibody directed against the poly-histidine tail.

As already specified, step a) of the screening method according to the invention encompasses determination of the ability of the candidate compound to modulate the interaction between the Tau polypeptide and the FKBP52 polypeptide as above defined by fluorescence assays using FRET. Thus, in a particular embodiment, the first Tau polypeptide as above defined is labelled with a first fluorophore substance and the second FKBP52 polypeptide is labelled with a second fluorophore substance. The first fluorophore substance may have a wavelength value that is substantially equal to the excitation wavelength value of the second fluorophore, whereby the bind of said first and second polypeptides is detected by measuring the fluorescence signal intensity emitted at the emission wavelength of the second fluorophore substance. Alternatively, the second fluorophore substance may also have an emission wavelength value of the first fluorophore, whereby the binding of said and second polypeptides is detected by measuring the fluorescence signal intensity emitted at the wavelength of the first fluorophore substance.

The fluorophores used may be of various suitable kinds, such as the well-known lanthanide chelates. These chelates have been described as having chemical stability, long-lived fluorescence (greater than 0.1 ms lifetime) after bioconjugation and significant energy-transfer in specificity bioaffinity assay. Document U.S. Pat. No. 5,162,508 discloses bipyridine cryptates. Polycarboxylate chelators with TEKES type photosensitizers (EP0203047A1) and terpyridine type photosensitizers (EP0649020A1) are known. Document WO96/00901 discloses diethylenetriaminepentaacetic acid (DPTA) chelates which used carbostyril as sensitizer. Additional DPT chelates with other sensitizer and other tracer metal are known for diagnostic or imaging uses (e.g., EP0450742A1).

In a preferred embodiment, the fluorescence assay performed at step a) of the screening method consists of a Homogeneous Time Resolved Fluorescence (HTRF) assay, such as described in document WO 00/01663 or U.S. Pat. No. 6,740,756, the entire content of both documents being herein incorporated by reference. HTRF is a TR-FRET based technology that uses the principles of both TRF (time-resolved fluorescence) and FRET. More specifically, the one skilled in the are may use a HTRF assay based on the time-resolved amplified cryptate emission (TRACE) technology as described in Leblanc et al. (2002). The HTRF donor fluorophore is Europium Cryptate, which has the long-lived emissions of lanthanides coupled with the stability of cryptate encapsulation. XL665, a modified allophycocyanin purified from red algae, is the HTRF primary acceptor fluorophore. When these two fluorophores are brought together by a biomolecular interaction, a portion of the energy captured by the Cryptate during excitation is released through fluorescence emission at 620 nm, while the remaining energy is transferred to XL665. This energy is then released by XL665 as specific fluorescence at 665 nm Light at 665 nm is emitted only through FRET with Europium. Because Europium Cryptate is always present in the assay, light at 620 nm is detected even when the biomolecular interaction does not bring XL665 within close proximity Therefore in one embodiment, step a) of the screening method may therefore comprises the steps consisting of:
(1) bringing into contact a pre-assay sample comprising:
a first Tau polypeptide fused to a first antigen,
a second FKBP52 polypeptide fused to a second antigen
a candidate compound to be tested
(2) adding to the said pre assay sample of step (2):
at least one antibody labelled with a European Cryptate which is specifically directed against the first said antigen
at least one antibody labelled with XL665 directed against the second said antigen
(3) illuminating the assay sample of step (2) at the excitation wavelength of the said European Cryptate
(4) detecting and/or quantifying the fluorescence signal emitted at the XL665 emission wavelength
(5) comparing the fluorescence signal obtained at step (4) to the fluorescence obtained wherein pre assay sample of step (1) is prepared in the absence of the candidate compound to be tested.

If at step (5) as above described, the intensity value of the fluorescence signal is different (lower or higher) than the intensity value of the fluorescence signal found when pre assay sample of step (1) is prepared in the absence of the candidate compound to be tested, then the candidate compound may be positively selected at step b) of the screening method.

Antibodies labelled with a European Cryptate or labelled with XL665 can be directed against different antigens of interest including GST, poly-histidine tail, DNP, c-myx, HA antigen and FLAG which include. Such antibodies encompass those which are commercially available from CisBio (Bedfors, Mass., USA), and notably those referred to as 61GSTKLA or 61HISKLB respectively.

In a particular embodiment, the methods of the invention may further comprise a step consisting of determining the ability of the candidate compound to modulate the interaction between a Amyloid Precursor Protein (APP) polypeptide and a FKBP52 polypeptide. Indeed a recent study have demonstrated that FKBP52 formed stable complexes with APP through its FK506 interacting domain. This study studies identify a novel role for FKBP52 in modulating toxicity of Abeta peptides (Sanokawa-Akakura R, Cao W, Allan K, Patel K, Ganesh A, Heiman G, Burke R, Kemp F W, Bogden J D, Camakaris J, Birge R B, Konsolaki M. Control of Alzheimer's amyloid beta toxicity by the high molecular weight immunophilin FKBP52 and copper homeostasis in *Drosophila*. PLoS One. 2010 January 13; 5 (1):e8626.). Accordingly, compounds that modulate both interaction between Tau and FKBP52 and interaction between APP and FKBP52 may be useful for the treatment of Alzheimer's disease.

In Cellulo Screening Methods of the Invention

The candidate compounds that have been positively selected at the end of any one of the embodiments of the in vitro screening which has been described previously in the present specification may be subjected to further selection steps in view of further assaying its properties on the Tau mediated cellular functions (such as tubulin polymerisation), Tau accumulation, Tau aggregation and all the post-translational Tau modifications. For this purpose, the candidate compounds that have been positively selected with the general in vitro screening method as above described may be further selected for their ability modulates the Tau mediated cellular functions, Tau accumulation, Tau aggregation and all the post-translational Tau modifications.

Thus another aspect of the invention relates to a method for screening a drug for the prevention and treatment of neurological disorders involving Tau dysfunction, wherein said method comprises the steps of:
i) screening for compounds that modulate the interaction between the Tau and the FKBP52 proteins, by performing the in vitro screening method according to any of claims 1 to 6 and
ii) screening the compounds positively selected at the end of step i) for their Tau mediated cellular functions, Tau accumulation, Tau aggregation and all the post-translational Tau modifications.

In certain preferred embodiments of the screening method above, step ii) of said screening method comprises the following steps:
(1) bringing into contact a cell with a compound that has been positively selected at the end of step i)
(2) determining the capacity of compound to modulate the Tau mediated cellular functions, Tau accumulation, Tau aggregation and all the post-translational Tau modifications
(3) comparing the Tau mediated cellular functions, Tau accumulation, Tau aggregation and all the post-translational Tau modifications determined at step (2) with the Tau mediated cellular functions, Tau accumulation, Tau aggregation and all the post-translational Tau modifications that are determined when step (1) is performed in the absence of the said positively selected compound.

For performing step (1), any cell may be suitable but neurons are preferred.

Step (1) as above described may be performed by adding an amount of the candidate compound to be tested to the culture medium. Usually, a plurality of culture samples are prepared, so as to add increasing amounts of the candidate compound to be tested in distinct culture samples. Generally, at least one culture sample without candidate compound is also prepared as a negative control for further comparison. Optionally, at least one culture sample with an already known agent that modulates the Tau mediated cellular functions, Tau accumulation, Tau aggregation and all the post-translational Tau modifications is also prepared as a positive control for standardisation of the method.

Therefore, step (3) may be performed by comparing the percentage of cells wherein the Tau mediated cellular functions, Tau accumulation, Tau aggregation and all the post-translational Tau modifications are modulated obtained for the cell cultures incubated with the candidate compound to be tested with the percentage of cells wherein the Tau mediated cellular functions, Tau accumulation, Tau aggregation and all the post-translational Tau modifications are modulated obtained for the negative control cell cultures without the said candidate compound. Illustratively, the efficiency of the candidate compound may be assessed by comparing (i) the percentage of cells wherein the Tau mediated cellular functions, Tau accumulation, Tau aggregation and all the post-translational Tau modifications are modulated measured in the cell cultures that were incubated therewith with (ii) the percentage of cells wherein the Tau mediated cellular functions, Tau accumulation, Tau aggregation and all the post-translational Tau modifications are modulated measured in the supernatant of the cell cultures that were incubated with the known agent that modulates the Tau mediated cellular functions, Tau accumulation, Tau aggregation and all the post-translational Tau modifications. Further illustratively, the efficiency of the candidate compound may be assessed by determining for which amount of the candidate compound added to the cell cultures the percentage of cells wherein the Tau mediated cellular functions, Tau accumulation, Tau aggregation and all the post-translational Tau modifications are modulated is close or higher than the percentage of cells wherein the Tau mediated cellular functions, Tau accumulation, Tau aggregation and all the post-translational Tau modifications are modulated measured with the known agent that modulates the Tau mediated cellular functions, Tau accumulation, Tau aggregation and all the post-translational Tau modifications.

Candidate Compounds of the Invention

According to a one embodiment of the invention, the candidate compound of may be selected from the group consisting of peptides, petptidomimetics, small organic molecules, antibodies, aptamers or nucleic acids. For example the candidate compound according to the invention may be selected from a library of compounds previously synthesised, or a library of compounds for which the structure is determined in a database, or from a library of compounds that have been synthesised de novo.

In a particular embodiment, the candidate compound may be selected form small organic molecules.

As used herein, the term "small organic molecule" refers to a molecule of size comparable to those organic molecules generally sued in pharmaceuticals. The term excludes biological macromolecules (e.g.; proteins, nucleic acids, etc.); preferred small organic molecules range in size up to 2000 da, and most preferably up to about 1000 Da.

The candidate compounds according to the invention may be selected from molecules that neutralize the PPIase activity of FKBP52 by interfering with its synthesis, translation and ligand/substrate/product-binding.

In a preferred embodiment, the molecules are selected from PPIase ligands of domain I of Protein FKBP52, preferably PPIase ligands preventing, blocking or inhibiting the PPIase activity of domain I of Protein FKBP52.

Advantageously, the molecules of the invention may prevent/inhibit/block the PPIase activity of domain I of Protein FKBP52 without inducing immunosuppressive activity.

A first series of the molecules are derivatives of FK 506 that are lacking immunosuppresive activity. FK 506 is represented hereunder:

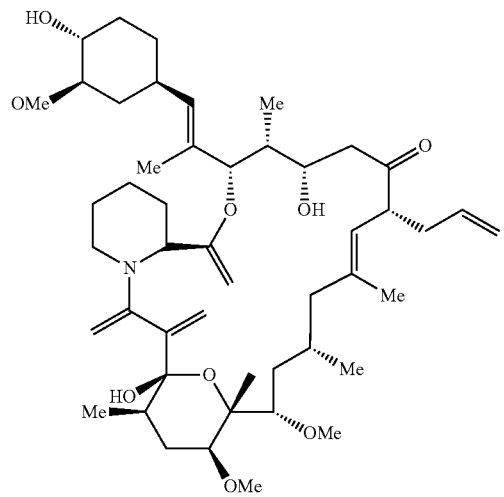

One particularly preferred family of molecules may consist of novel analogues of the neurophilin compound represented below also named as VA-10367 (Vertex, Inc):

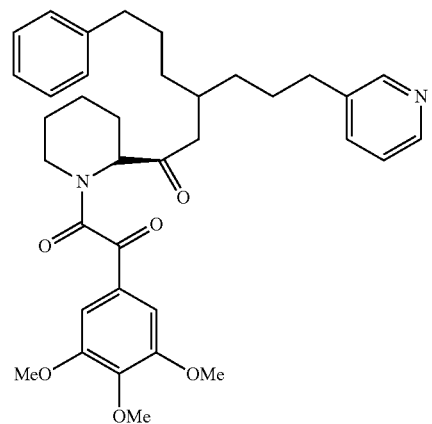

Other examples include derivatives of Rapamycin lacking the immunosuppressant activity, such as Meridamycin as described in the International Patent Application Publication n° WO2005084673. Other derivatives of Rapamycin include those described in Ruan B. et al. (Ruan B, Pong K, Jow F, Bowlby M, Crozier R A, Liu D, Liang S, Chen Y, Mercado M L, Feng X, Bennett F, von Schack D, McDonald L, Zaleska M M, Wood A, Reinhart P H, Magolda R L, Skotnicki J, Pangalos M N, Koehn F E, Carter G T, Abou-Gharbia M, Graziani E I. Binding of rapamycin analogs to calcium channels and FKBP52 contributes to their neuroprotective activities. Proc Natl Acad Sci USA. 2008 January 8; 105(1):33-8. Epub 2007 Dec. 27.) such as WYE-592 or ILS-290:

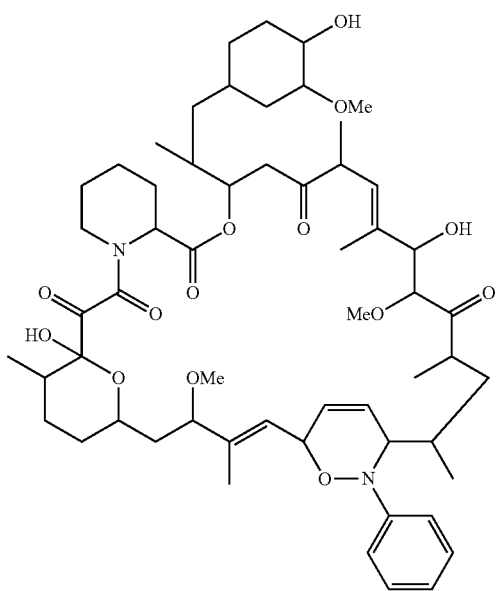

WYE-592

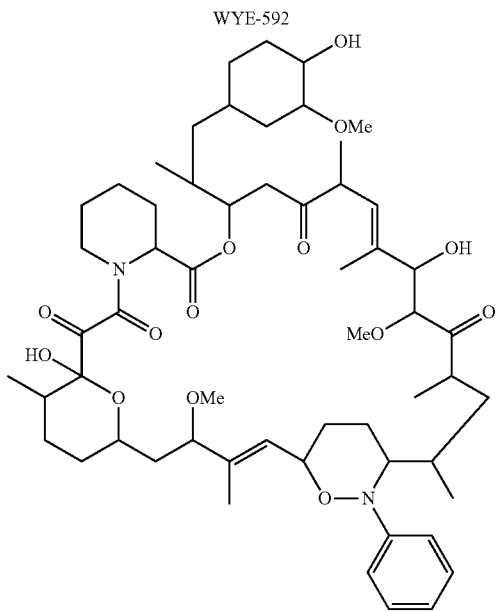

ILS-90

The molecules of the invention may be synthesized by any conventional method well known to the skilled person.

In another particular embodiment, the candidate compounds according to the invention may be antibodies o specifically directed to the interaction site between protein Tau and protein FKBP52 or impacting the FKBP52-Tau interaction and/or its functional cellular functions.

The term "antibody" or "antibodies" relates to an antibody characterized as being specifically directed to the interaction site of FKBP52 with Tau, or any functional derivative thereof, with above mentioned antibodies being preferably monoclonal antibodies; or an antigen-binding fragment thereof, of the F(ab')2, or single chain Fv type, or any type of recombinant antibody derived thereof. These antibodies of the invention include specific polyclonal antisera prepared against the interaction site of FKBP52 with Tau.

The antibodies of the invention can for instance be produced by any hybridoma liable to be formed according to classical methods from splenic cells of an animal, particularly of a mouse or rat immunized against the peptidic sequence involved in the interaction between Tau and FKBP52 or any functional derivative thereof, and of cells of a myeloma cell line, and to be selected by the ability of the hybridoma to produce the monoclonal antibodies recognizing the peptidic sequence involved in the interaction between Tau and FKBP52 or any functional derivative thereof which have been initially used for the immunization of the animals. The antibodies according to this embodiment of the invention may be humanized versions of the mouse antibodies made by means of recombinant DNA technology, departing from the mouse and/or human genomic DNA sequences coding for H and L chains or from cDNA clones coding for H and L chains.

Alternatively the antibodies according to this embodiment of the invention may be human antibodies. Such human antibodies are prepared, for instance, by means of human peripheral blood lymphocytes (PBL) repopulation of severe combined immune deficiency (SCID) mice as described in PCT/EP 99/03605 or by using transgenic non-human animals capable of producing human antibodies as described in U.S. Pat. No. 5,545,806. Also fragments derived from these antibodies such as Fab, F (ab)'2 ands ("single chain variable fragment"), providing they have retained the original binding properties, form part of the present invention. Such fragments are commonly generated by, for instance, enzymatic digestion of the antibodies with papain, pepsin, or other proteases. It is well known to the person skilled in the art that monoclonal antibodies or fragments thereof, can be modified for various uses. An appropriate label of the enzymatic, fluorescent, or radioactive type can label the antibodies involved in the invention.

In another particular embodiment, the candidate compounds according to the invention may be selected from aptamers. Aptamers are a class of molecule that represents an alternative to antibodies in term of molecular recognition. Aptamers are oligonucleotide or oligopeptide sequences with the capacity to recognize virtually any class of target molecules with high affinity and specificity. Such ligands may be isolated through Systematic Evolution of Ligands by EXponential enrichment (SELEX) of a random sequence library, as described in Tuerk C. and Gold L., 1990. The random sequence library is obtainable by combinatorial chemical synthesis of DNA. In this library, each member is a linear oligomer, eventually chemically modified, of a unique sequence. Possible modifications, uses and advantages of this class of molecules have been reviewed in Jayasena S. D., 1999. Peptide aptamers consists of a conformationally constrained antibody variable region displayed by a platform protein, such as E. coli Thioredoxin A that are selected from combinatorial libraries by two hybrid methods (Colas et al., 1996).

In another embodiment, the candidate molecules may be selected from molecules that block the synthesis of Protein FKBP52.

By synthesis is meant the transcription of the FKBP52 gene. Small molecules can bind on the promoter region of the FKBP52 and inhibit binding of a transcription factor or these molecules can bind a transcription factor and inhibit binding to the FKBP52-promoter so that there is no expression of the FKBP52.

Also within the scope of the invention is the use of oligoribonucleotide sequences that include anti-sense RNA and DNA molecules and ribozymes that function to inhibit the translation of FKBP52 mRNA. Anti-sense RNA and DNA molecules act to directly block the translation of mRNA by binding to targeted mRNA and preventing protein translation. In regard to antisense DNA, oligodeoxyribonucleotides derived from the translation initiation site. Ribozymes are enzymatic RNA molecules capable of catalysing the specific cleavage of RNA. The mechanism of ribozyme action involves sequence specific hybridisation of the ribozyme molecule to complementary target RNA, followed by an endonucleolytic To inhibit the activity of the gene or the gene product of FKBP52 custom-made techniques are available directed at three distinct types of targets: DNA, RNA and protein; For example, the gene or gene product of FKBP52 can be altered by homologous recombination, the expression of the genetic code can be inhibited at the RNA levels by antisense oligonucleotides, interfering RNA (RNAi) or ribozymes, and the protein function can be altered by antibodies or drugs.

Another embodiment of present invention is the use of a molecule that inhibits the expression of FKBP52 and preferably a molecule that inhibits the expression of FKBP52 selected from the list consisting of an antisense molecule, a RNAi and a ribozyme, for the manufacture of a drug to prevent or treat a disorder of Tau aggregation or deposition in neurofibrillary tangles in a subject in need thereof.

Methods of Treatment of the Invention

In a further aspect, the invention provides a method for the prevention and treatment of neurological disorders involving Tau dysfunction comprising administering a subject in need thereof with a therapeutically effective amount of a compound that modulate the interaction between the Tau and the FKBP52 protein. Said compound may be identified by the screening methods of the invention.

More particularly, the invention relates to a compound that modulates the interaction between the Tau and the FKBP52 protein for use in the prevention and treatment of neurological disorders involving Tau dysfunction.

The methods of the invention are useful for the prevention and treatment of neurological disorders involving Tau dysfunction including Alzheimer's disease, frontotemporal dementia, progressive supranuclear palsy, corticobasal degeneration and frontotemporal lobar degeneration, also known as Pick's disease, as well as all neurological disorders which might, in the future, prove to involve Tau, such as the Parkinson disease for instance.

According to the invention, the term "patient" or "patient in need thereof", is intended for a human or non-human mammal (e.g. dog, cat, horses . . . ) affected or likely to be affected with neurological disorders involving Tau dysfunction.

By a "therapeutically effective amount" of the compound of the invention is meant a sufficient amount of compound to treat neurological disorders involving Tau dysfunction, at a reasonable benefit/risk ratio applicable to any medical treatment. It will be understood, however, that the total daily usage of the compound of the invention and compositions of the present invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed, the age, body weight, general health, sex and diet of the patient; the time of administration, route of administration, and rate of excretion of the specific compound employed; the duration of the treatment; drugs used in combination or coincidental with the specific compound employed; and like factors well known in the medical arts. For example, it is well within the skill of the art to start doses of the compound at levels lower than those required to achieve the desired therapeutic effect and to gradually increase the dosage until the desired effect is achieved.

The compound that modulates the interaction between the Tau and the FKBP52 protein of the invention may be combined with pharmaceutically acceptable excipients. "Pharmaceutically" or "pharmaceutically acceptable" refers to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type.

In a further aspect, the invention provides a method for the prevention and treatment of Alzheimer's disease comprising administering a subject in need thereof with a therapeutically effective amount of a compound that modulate both the interaction between the Tau and the FKBP52 protein and the interaction between FKBP52 and APP.

Diagnostic Methods of the Invention

A further aspect of the invention pertains to diagnostic, prognostic, and monitoring assays.

Accordingly, in a particular embodiment, the invention relates to a method of testing a subject thought to have or be predisposed to having a neurological disorders involving Tau dysfunction, which comprises the step of analyzing a sample of interest obtained from said subject for measuring the level of the complex between FKBP52 protein and Tau protein.

As used herein, the term "sample of interest" include encompasses a variety of sample types obtained from a subject and can be used in a diagnostic assay. Samples herein may be any type of sample, such as any cell samples, biological fluids including, blood, serum, urine, spinal fluid . . . or any biopsy sample obtained from a subject's tissue. In a preferred embodiment, the sample of interest is a spinal fluid sample.

In a particular embodiment, the methods of the invention comprise contacting the sample of interest with a binding partner capable of selectively interacting with the complex between FKBP52 protein and Tau protein present in the sample of interest. In another particular embodiment, methods of the invention comprise may involve contacting the sample of interest with a binding partner capable of selectively interacting with the FKBP52 protein and another binding partner capable of selectively interacting Tau protein present in the sample of interest.

The binding partners according to the invention may be an antibody that may be polyclonal or monoclonal, preferably monoclonal. In another embodiment, the binding partner may be an aptamer.

The binding partners of the invention such as antibodies or aptamers, may be labelled with a detectable molecule or substance, such as a fluorescent molecule, a radioactive molecule or any others labels known in the art. Labels are known in the art that generally provide (either directly or indirectly) a signal.

As used herein, the term "labelled", with regard to the antibody, is intended to encompass direct labelling of the antibody or aptamer by coupling (i.e., physically linking) a detectable substance, such as a radioactive agent or a fluorophore (e.g. fluorescein isothiocyanate (FITC) or phycoerythrin (PE) or Indocyanine (Cy5)) to the antibody or aptamer, as well as indirect labelling of the probe or antibody by reactivity with a detectable substance. An antibody or aptamer of the invention may be labelled with a radioactive molecule by any method known in the art. For example radioactive molecules include but are not limited radioactive atom for scintigraphic studies such as I123, I124, In111, Re186, Re188.

The aforementioned assays generally involve the bounding of the binding partner (ie. Antibody or aptamer) in a solid support. Solid supports which can be used in the practice of the invention include substrates such as nitrocellulose (e.g., in membrane or microtiter well form); polyvinylchloride (e.g., sheets or microtiter wells); polystyrene latex (e.g., beads or microtiter plates); polyvinylidine fluoride; diazotized paper; nylon membranes; activated beads, magnetically responsive beads, and the like.

The level of the complex between FKBP52 protein and Tau protein may be measured by using standard immunodiagnostic techniques, including immunoassays such as competition, direct reaction, or sandwich type assays. Such assays include, but are not limited to, agglutination tests; enzyme-labelled and mediated immunoassays, such as ELISAs; biotin/avidin type assays; radioimmunoassays; immunoelectrophoresis; immunoprecipitation.

More particularly, an ELISA method can be used, wherein the wells of a microtiter plate are coated with a set of binding partners according to the invention. A sample of interest containing or suspected of containing the complex between FKBP52 protein and Tau protein is then added to the coated wells. After a period of incubation sufficient to allow the formation of antibody-antigen complexes, the plate(s) can be washed to remove unbound moieties and a detectably labelled secondary binding molecule added. The secondary binding molecule is allowed to react with any captured sample marker protein, the plate washed and the presence of the secondary binding molecule detected using methods well known in the art.

Alternatively an immunohistochemistry (IHC) method may be preferred. IHC specifically provides a method of detecting targets in a tissue specimen in situ. The overall cellular integrity of the sample of interest is therefore maintained in IHC, thus allowing detection of both the presence and location of the complex between FKBP52 protein and Tau protein. Typically the sample is fixed with formalin, embedded in paraffin and cut into sections for staining and subsequent inspection by light microscopy. Current methods of IHC use either direct labeling or secondary antibody-based or hapten-based labeling. Examples of known IHC systems include, for example, EnVision™ (DakoCytomation), Powervision® (Immunovision, Springdale, Ariz.), the NBA™ kit (Zymed Laboratories Inc., South San Francisco, Calif.), HistoFine® (Nichirei Corp, Tokyo, Japan).

In particular embodiment, a tissue section may be mounted on a slide or other support after incubation with the binding partners of the invention d. Then, microscopic inspections in the sample mounted on a suitable solid support may be performed. For the production of photomicrographs, sections comprising samples may be mounted on a glass slide or other planar support, to highlight by selective staining the presence of the proteins of interest.

Therefore IHC samples may include, for instance: (a) preparations comprising a cell sample or a tissue sample (b) fixed and embedded said cells and (c) detecting the complex between FKBP52 protein and Tau protein in said cells samples. In some embodiments, an IHC staining procedure may comprise steps such as: cutting and trimming tissue, fixation, dehydration, paraffin infiltration, cutting in thin sections, mounting onto glass slides, baking, deparaffination, rehydration, antigen retrieval, blocking steps, applying primary antibodies, washing, applying secondary antibodies (optionally coupled to a suitable detectable label), washing, counter staining, and microscopic examination.

In one embodiment, the method of the invention further may comprise a step of comparing the level of the complex between FKBP52 protein and Tau protein with a predetermined threshold value. Said comparison is indicative whether the subject is thought to have or be predisposed to having a neurological disorders involving Tau dysfunction. The predetermined value may refer to the amount of the complex between FKBP52 protein and Tau protein in sample of interests obtained from the general population or from a select population of subjects. For example, the select population may be comprised of apparently healthy subjects, such as individuals who have not previously had any sign or symptoms indicating the presence of neurological disorders involving Tau dysfunction. In another example, the predetermined value may be comprised of subjects having established neurological disorders involving Tau dysfunction. The predetermined value can be a cut-off value, or a range. The predetermined value can be established based upon comparative measurements between apparently healthy subjects and subjects with established neurological disorders involving Tau dysfunction.

Moreover, without wishing to be bound by theory, the inventors believe that aberrant expression or activity of FKBP52, and/or especially its ability to bind Tau thereby determine whether an individual is afflicted with a neurological disorders involving Tau dysfunction, or is at risk of developing a neurological disorders involving Tau dysfunction.

Accordingly, in a particular embodiment, the invention relates to a method of testing a subject thought to have or be predisposed to having a neurological disorders involving Tau dysfunction, which comprises the step of analyzing a sample of interest obtained from said subject for detecting the presence of a mutation in the gene encoding for FKBP52 protein and/or its associated promoter.

Typical techniques for detecting a mutation in the gene encoding for FKBP52 protein may include restriction fragment length polymorphism, hybridisation techniques, DNA sequencing, exonuclease resistance, microsequencing, solid phase extension using ddNTPs, extension in solution using ddNTPs, oligonucleotide assays, methods for detecting single nucleotide polymorphism such as dynamic allele-specific hybridisation, ligation chain reaction, mini-sequencing, DNA "chips", allele-specific oligonucleotide hybridisation with single or dual-labelled probes merged with PCR or with molecular beacons, and others.

In another particular embodiment, the invention relates to a method of testing a subject thought to have or be predisposed to having a neurological disorders involving Tau dysfunction, which comprises the step of analyzing a sample of interest obtained from said subject for analyzing the expression of the gene encoding for FKBP52 protein.

Analyzing the expression of the gene encoding for FKBP52 protein may be assessed by any of a wide variety of well-known methods for detecting expression of a transcribed nucleic acid or translated protein.

In a preferred embodiment, the expression of the gene encoding for FKBP52 protein is assessed by analyzing the expression of mRNA transcript or mRNA precursors, such as nascent RNA, of said gene. Said analysis can be assessed by preparing mRNA/cDNA from cells in a sample of interest from a subject, and hybridizing the mRNA/cDNA with a reference polynucleotide. The prepared mRNA/cDNA can be used in hybridization or amplification assays that include, but are not limited to, Southern or Northern analyses, polymerase chain reaction analyses, such as quantitative PCR (TaqMan), and probes arrays such as GeneChip™ DNA Arrays (AFF-YMETRIX).

Advantageously, the analysis of the expression level of mRNA transcribed from the gene encoding for FKBP52 protein involves the process of nucleic acid amplification, e.g., by RT-PCR (the experimental embodiment set forth in U.S. Pat. No. 4,683,202), ligase chain reaction (BARANY, Proc. Natl. Acad. Sci. USA, vol. 88, p: 189-193, 1991), self sustained sequence replication (GUATELLI et al., Proc. Natl. Acad. Sci. USA, vol. 57, p: 1874-1878, 1990), transcriptional amplification system (KWOH et al., 1989, Proc. Natl. Acad. Sci. USA, vol. 86, p: 1173-1177, 1989), Q-Beta Replicase (LIZARDI et al., Biol. Technology, vol. 6, p: 1197, 1988), rolling circle replication (U.S. Pat. No. 5,854,033) or any other nucleic acid amplification method, followed by the detection of the amplified molecules using techniques well known to those of skill in the art. These detection schemes are especially useful for the detection of nucleic acid molecules if such molecules are present in very low numbers. As used herein, amplification primers are defined as being a pair of nucleic acid molecules that can anneal to 5' or 3'regions of a gene (plus and minus strands, respectively, or vice-versa) and contain a short region in between. In general, amplification primers are from about 10 to 30 nucleotides in length and flank a region from about 50 to 200 nucleotides in length. Under appropriate conditions and with appropriate reagents, such primers permit the amplification of a nucleic acid molecule comprising the nucleotide sequence flanked by the primers.

In another particular embodiment, the invention relates to a method of testing a subject thought to have or be predisposed to having a neurological disorders involving Tau dysfunction, which comprises the step of analyzing a sample of interest obtained from said subject for measuring the concentration of FKBP52 protein.

Measuring the concentration of the FKBP52 protein may be assessed by using a binding partner as above described, and more particularly an antibody (e.g., a radio-labeled, chromophore-labeled, fluorophore-labeled, or enzyme-labeled antibody), an antibody derivative (e.g., an antibody conjugate with a substrate or with the protein or ligand of a protein of a protein/ligand pair (e.g., biotin-streptavidin)), or an antibody fragment (e.g., a single-chain antibody, an isolated antibody hypervariable domain, etc.) which binds specifically to the FKBP52 protein.

Said analysis can be assessed by a variety of techniques well known from one of skill in the art including, but not limited to, enzyme immunoassay (EIA), radioimmunoassay (RIA), Western blot analysis and enzyme linked immunoabsorbant assay (RIA).

The methods of the invention may comprise comparing the level of expression of the gene encoding for FKBP52 protein or the concentration of the FKBP52 protein in the sample of interest from a subject with a predetermined threshold value. The predetermined value may refer to the expression level or concentration measured in sample of interests obtained from the general population or from a select population of subjects. For example, the select population may be comprised of apparently healthy subjects, such as individuals who have not previously had any sign or symptoms indicating the presence of neurological disorders involving Tau dysfunction. In another example, the predetermined value may be comprised of subjects having established neurological disorders involving Tau dysfunction. The predetermined value can be a cut-off value, or a range. The predetermined value can be established based upon comparative measurements between apparently healthy subjects and subjects with established neurological disorders involving Tau dysfunction.

In another particular embodiment, the invention relates to a method of testing a subject thought to have or be predisposed to having a neurological disorders involving Tau dysfunction, which comprises the step of analyzing a sample of interest obtained from said subject for detecting post-translational modifications of FKBP52 protein.

The post-translational modifications FKBP52 protein include but are not limited to phosphorylation, acetylation, glycosylation. and the like. Detecting the post-translational modifications of the FKBP52 protein may be assessed by using a binding partner specific for a post-translational form of FKBP52 protein. As described above, the binding partner may be an antibody (e.g., a radio-labeled, chromophore-labeled, fluorophore-labeled, or enzyme-labeled antibody), an antibody derivative (e.g., an antibody conjugate with a substrate or with the protein or ligand of a protein of a protein/ligand pair (e.g., biotin-streptavidin)), or an antibody fragment (e.g., a single-chain antibody, an isolated antibody hypervariable domain, etc.) which binds specifically to a specific form of the FKBP52 protein. Said analysis can be assessed by a variety of techniques well known from one of skill in the art including, but not limited to, enzyme immunoassay (EIA), radioimmunoassay (RIA), Western blot analysis and enzyme linked immunoabsorbant assay (RIA).

The methods as above described may then particularly suitable for the prognostic or predictive purpose to administer the subject with a prophylactic treatment prior to the onset of clinical signs characterized by or associated with a neurological disorders involving Tau dysfunction. Clinical signs may include but are not limited to any sort of dysfunction of any CNS activity (such as motor/sensitive activities, sleep disturbances, depressive states, amnesic troubles, etc. . . . ). More particularly, the methods of the invention may be also useful for monitoring the treatment of a subject affected with a neurological disorders involving Tau dysfunction.

The invention will be further illustrated by the following figures and examples. However, these examples and figures should not be interpreted in any way as limiting the scope of the present invention.

FIGURES

FIG. 1: FKBP52 in the brain. Twenty μg of cytosol proteins from different adult rat brain regions were analyzed by Western blotting using anti-FKBP52 antibody 761. Actin served as the loading control.

FIGS. 2A-D: Association between FKBP52 and Tau proteins. A) GST Pull-down assay: Immunoblot (IB) for Tau showing the binding of soluble microtubule extract proteins incubated with GST-tagged FKBP52, or GST alone as control. B) Co-immunoprecipitation assay: A soluble microtubule extract was subjected to immunoprecipitation (IP) with immunopurified anti-FKBP52 antibody, or pre-immune serum used as control. The supernatants (S) and precipitates (P) were immunoblotted with anti-Tau antibody (clone DC25). C) The ability of Tau proteins to bind FKBP52 directly was monitored by dot blot assay. Different amounts of recombinant Tau (hT40) were spotted onto nitrocellulose membranes and then assayed for bound FKBP52 (0.5 µg) using anti-FKBP52 antibody. 5 µg GST spotted onto nitrocellulose membrane were used as the control. D) Quantitation: 100% corresponds to 0.5 µg of FKBP52 loading before milk saturation, and 0% corresponds to 0.5 µg of FKBP52 loading after milk saturation. The background is defined as the signal when GST was loaded instead of hT40. The level of FKBP52 captured by hT40 was calculated after subtraction of background.

FIGS. 3A-C: Relevance of Tau phosphorylation for its interaction with FKBP52. A) Recombinant Tau (hT40), P-Tau and HP-Tau were analyzed by SDS-Page. Phosphorylation and hyperphosphorylation of HT40 resulted in a marked reduction in the gel mobility of recombinant Tau as shown on an immunoblot (IB), with anti-Tau antibody (clone DC25). B) Dot blot assay with 2.2 µg of HP-Tau (1), P-Tau (2), pure recombinant hT40 (3), to which had been added, just before spotting, the same amount of cytosol as used to generate P-Tau (4) or HP-Tau (5). Dot 6 refers to the GST (5 µg) load. C) Bar graph of results.

Figure 4A:
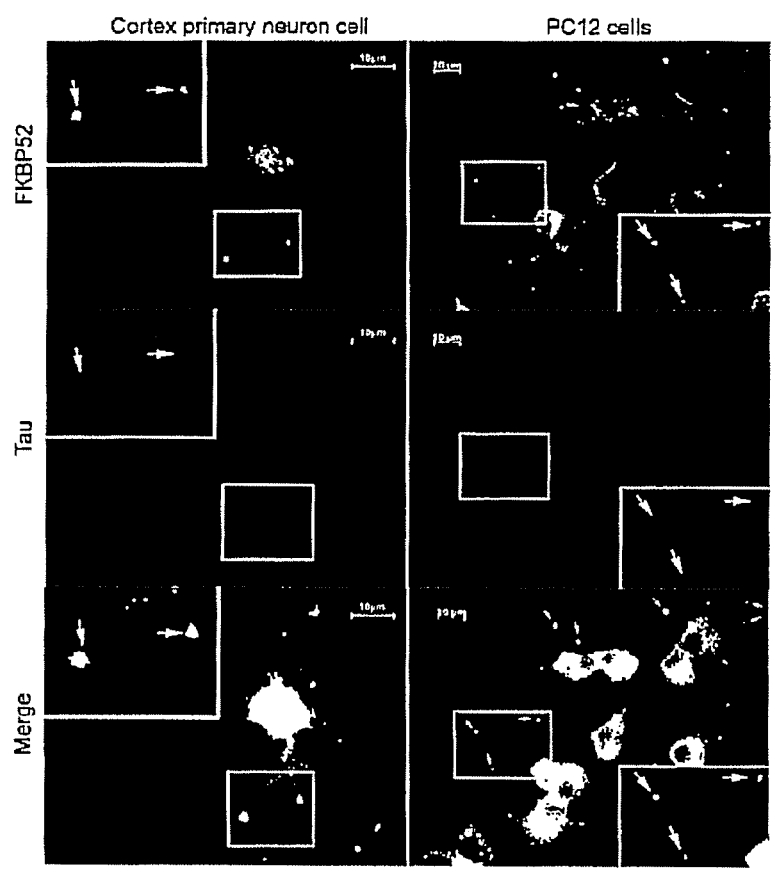
Figure 4B:
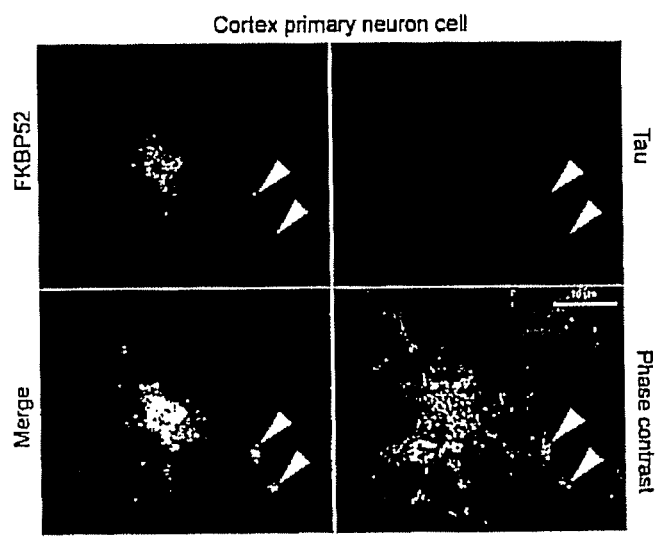
Figure 5A:
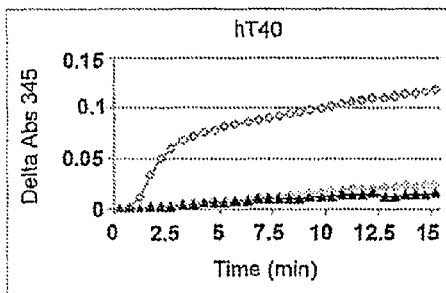
Figure 5B:
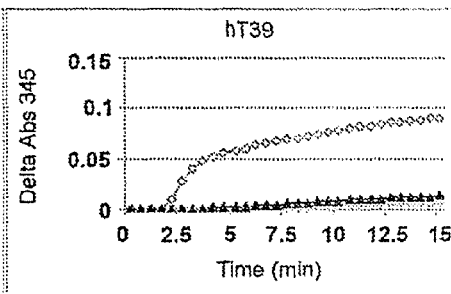
Figure 5C:
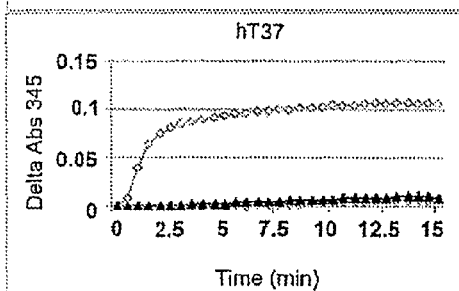
Figure 5D:
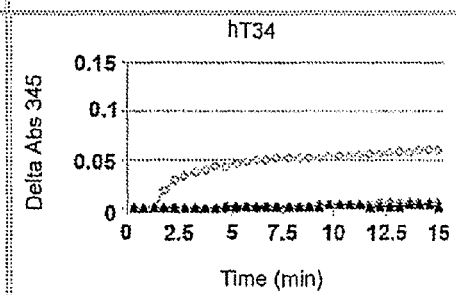
Figure 5E:
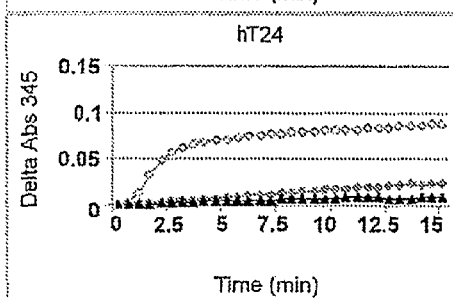
Figure 5F:
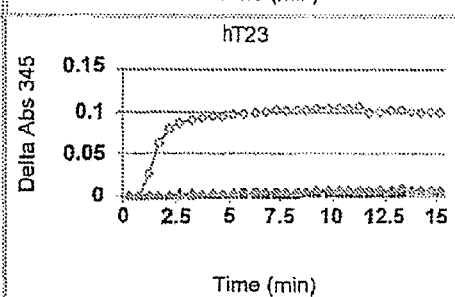
Figure 5G:
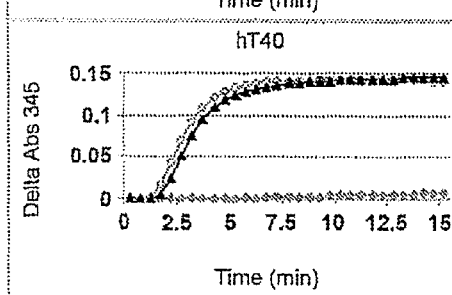
Figures 9A, 9B:
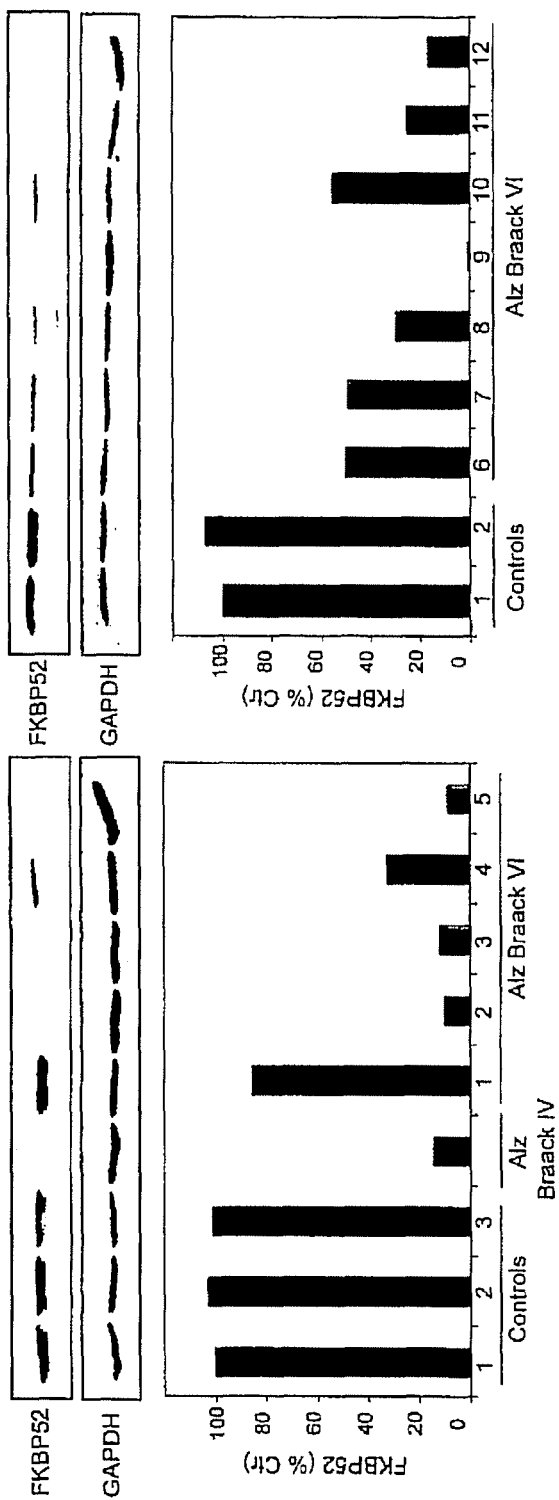
Figure 9C:
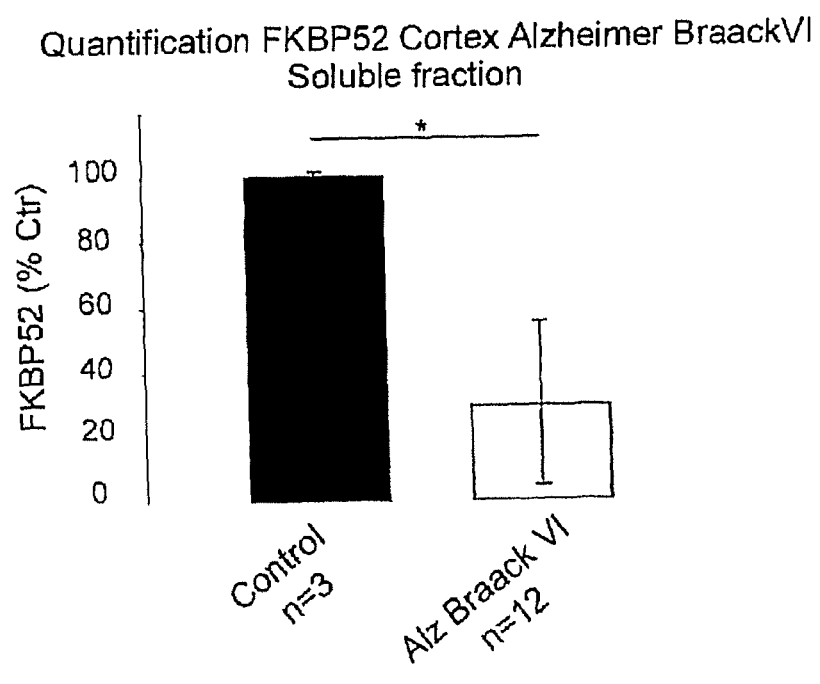
Figures 9D, 9E:
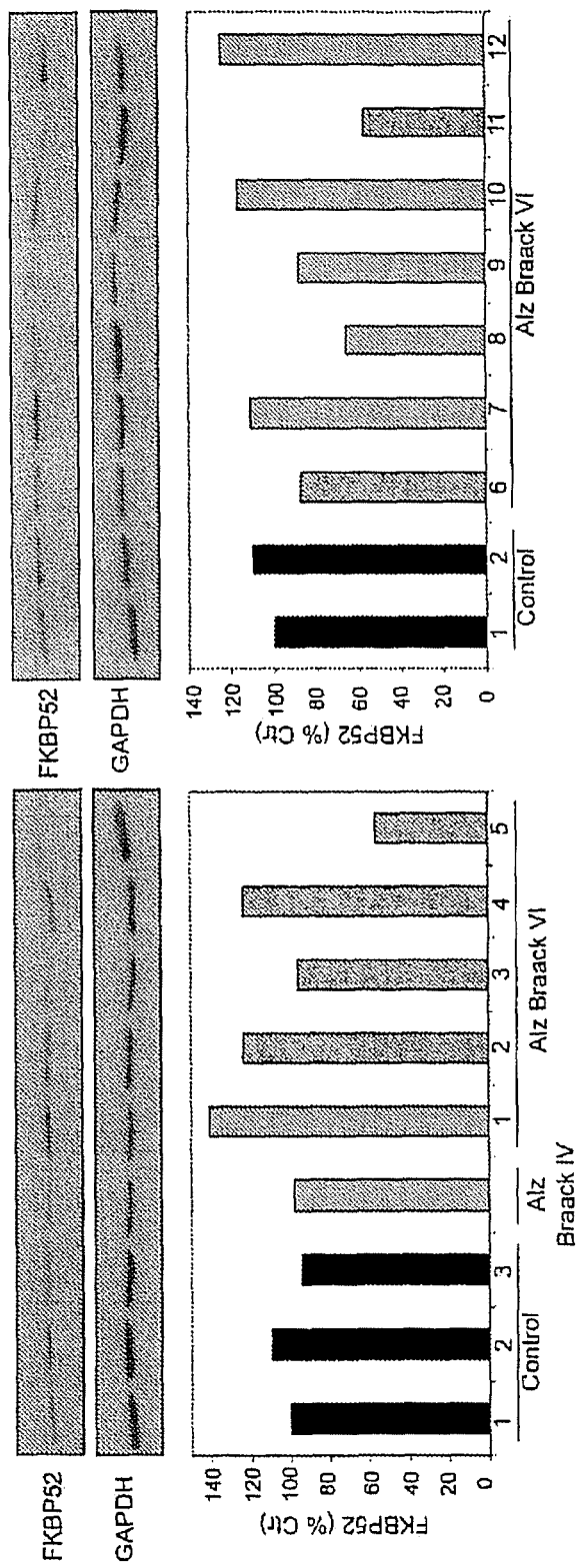
Figure 9F:
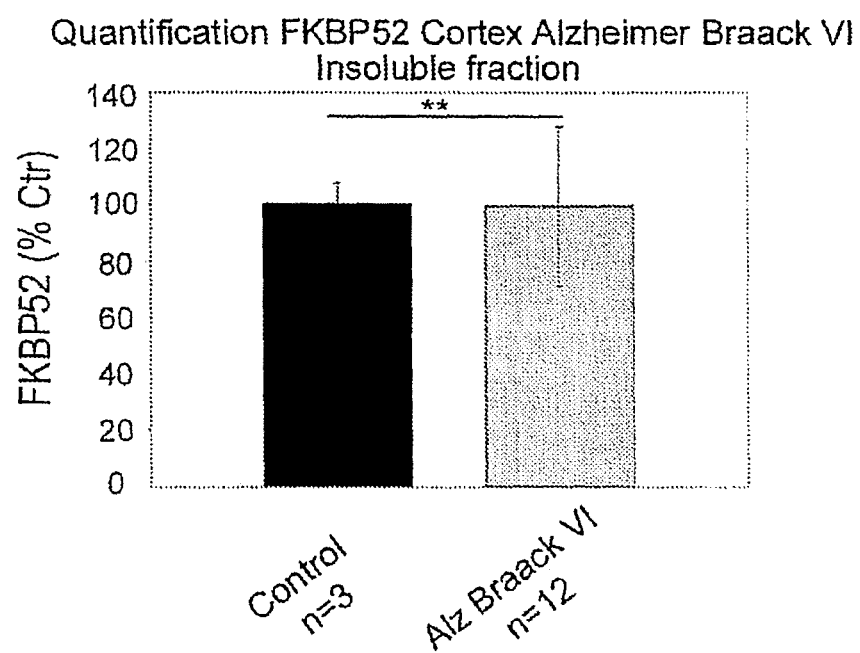

FIGS. 4A-B: Colocalization of FKBP52 and TAU in primary cortical neurons and PC12 cells. A) Immunofluorescence staining of primary cortical neurons and PC12 cells treated with 50 nM NGF for 5 days. Double staining for Tau and FKBP52 was performed after cytosol extraction to reveal cytoskeletal association. Arrows indicate preferential colocalization of both proteins in the distal part of the nerve cell axon and at the extremity of PC12 cell neurites.

B) Confocal images of primary cortical neurons. Double staining was performed as in (A). Analysis of 0.5 µm slices confirms the preferential colocalization in the distal part of the axon (see arrowheads)

FIGS. 5A-G: Effect of FKBP52 on tubulin polymerization induced by recombinant Tau isoforms. Tubulin polymerization was performed by switching the samples from 4° C. to 37° C. and the change in turbidity was monitored at 345 nm for 15 min Tubulin (1 mg/ml) purified from rat brain was incubated in the absence (♦) or presence of 1.7 µM (23 µg for HT40) different human Tau isoforms without FKBP52 (▲) or with 3.5 µM (55 µg) FKBP52 (◊) Tau isoforms differ from each other by the number of repeats in the microtubule binding domain and insertions in the N-terminal. The labelling of tau isoforms uses the published nomenclature (28). A: ht40, B: ht39, C: hT37, D: hT34, E: hT24, F: hT23, G: This control experiment was carried out as in (A), except that 3.5 µM GST (▲) was used instead of FKBP52.

FIGS. 6A-F: Effect of FKBP52 overexpression on Tau accumulation and neurite outgrowth A) PC12 cells treated or not with NGF (50 nM) in the absence or presence of 1 µg/ml Dox (doxycycline). Ten µg of total protein extracts were analyzed for FKBP52 levels by western blot using anti-FKBP52 antibody 761. B) The FKBP52 level was determined as in (A) in H7C2 cells treated or not with Dox. The use of rabbit FKBP52 as the exogenous protein explains the small difference in gel mobility with the endogenous rat protein. C) H7C2 and D) PC12 cells were treated or not with NGF for 5 days, in the presence or absence of Dox for one week; 50 µg of extracts was subjected to SDS-PAGE and immunoblotted with anti-Tau (antibody clone DC25). Actin was used as the loading control. E) Representative H7C2 cells in the presence of NGF (50 nM) with or without Dox. F) Neurite length was quantified from random photographs (see materials and methods). Similar results were obtained in 3 separate experiments. **: P<0.01 (Student-Newman-Keuls test, Anova).

FIGS. 7A-B: centrifugal sedimentation and western blot analysis of Tau polymerization: (A) in oxidative conditions: Ox (B) in reducing conditions: Red. S, Supernatants, P, Pellets.

FIG. 8: Centrifugal sedimentation and western blot analysis of Tau polymerization in oxidative conditions: recombinant Tau at 0.5 mg/ml 1: alone, 2: with FKBP52, 3: with GST. S, Supernatants, P, Pellets.

FIGS. 9A-F: Expression level of FKBP52 in Alzheimer disease and control brains. Western blot analysis of FKBP52 in soluble homogenate fraction from normal and Alzheimer disease. GAPDH was used as loading control. Intensities of the chemoluminescence were quantified with Image-J software. (A), soluble fractions 1-5; (B), soluble fractions 6-12; (C) soluble data combined; (D) insoluble fractions 1-5; (E), insoluble fractions 6-12; (F) insoluble data combined.

Figure 10A:
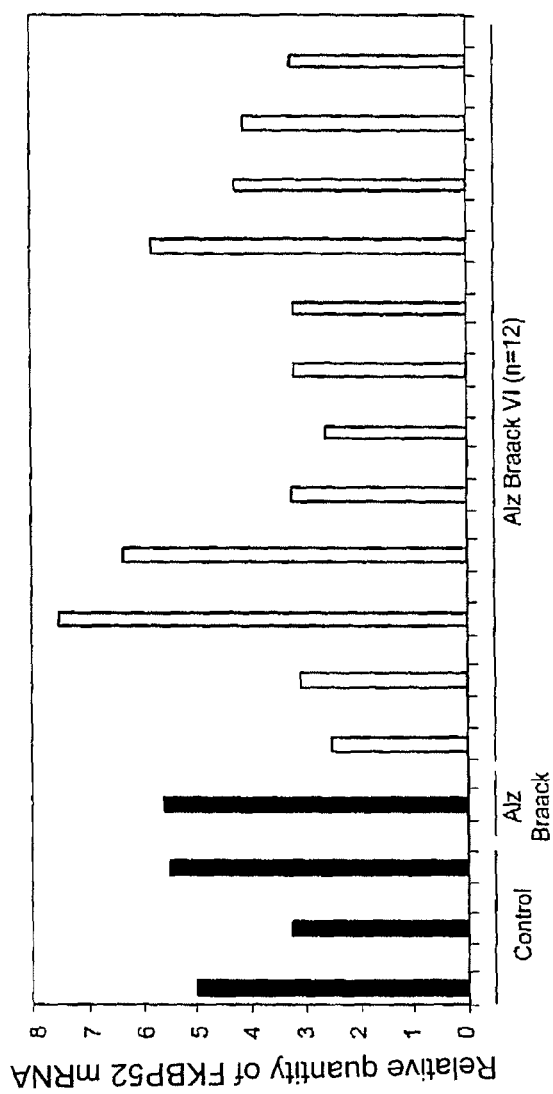

FIGS. 10A and B: Expression level of mRNA FKBP52 in Alzheimer disease and controls. Quantification of mRNA FKBP52 was carried out after normalisation with mRNA GAPDH. (A), individual samples; (B) combined data.

EXAMPLE 1

A Role For Fkbp52 In Tau Protein Function

Materials and Methods

Antibodies and reagents: Anti-Tau mAB (clone DC25) and anti-Tau mAB (Tau5) was from Sigma and Calbiochem respectively. Anti-FKBP52 pAB 761 was as described (9). GTP was from Sigma and doxycycline was from Clontech.

Preparation of Tubulin and microtubule assembly assay: Male adult Sprague-Dawley rats (body weight ~250 g) were obtained from Janvier (Le Genest-St.-Isle, France). They were killed by decapitation, according to institutional guidelines, and whole brains were used immediately to prepare tubulin as described (9). Microtubule assembly assays were performed as in (9).

Protein purification and Overexpression of different Tau isoforms and FKBP52 protein: The six isoforms of human brain Tau were expressed in E. coli from clones hT40, hT39, hT37, hT34, hT24, hT23 and purified as described (28). Full length FKBP52 was affinity purified as in (23). For the Tubulin polymerization assay, FKBP52 bound to glutathione-Sepharose beads (GE Healthcare) were cleaved overnight at 4° C. with 2 units of thrombin (GE Healthcare) and dialyzed against buffer L (0.1 M Mes, 1 mM EGTA, 1 mM $MgCL_2$, 0.1 mM EDTA) with 10% glycerol, and complemented before use to 1 mM GTP and 1 mM DTT and 10 µM PPACK (a potent irreversible inhibitor of thrombin) (Biomol).

Phosphorylation and hyperphosphorylation of recombinant Tau: Rat brain extract was used as the source of kinase activity, as described (18). Briefly, recombinant hT40 was incubated with cytosol of adult rat brain, in the presence or absence of okadaic acid, to give HP-Tau (hyperphosphorylated-Tau) and P-Tau (phosphorylated-Tau), respectively.

Protein binding assays: GST-pull down assay: 100 µl of glutathione-Sepharose beads preloaded with 1 nmol GST-FKBP52 or 1 nmol GST, were washed 4 times with 500 µl of buffer A (buffer L complemented with 1 mM DTT and 1 mM GTP) and then resuspended in the same buffer containing protein microtubule extract. The proteins were analyzed for the presence of Tau isoforms by SDS/PAGE western blot analysis using antibody anti-Tau (clone DC25) diluted 1/1000.

Coimmunoprecipitation assay: It was carried out with 1 mg cytosol microtubule extract as described (12).

Dot blot assay: 100 μl of buffer A containing different amounts of hT40 were applied to a nitrocellulose membrane, blocked with 5% non-fat milk in phosphate-buffered saline (PBS) containing 0.1% Tween 20 (PBS-T) at room temperature, washed with PBS-T and buffer A, followed by 2 h incubation at room temperature with 100 μl of buffer A containing 0.5 μs recombinant FKBP52. The membranes were washed with buffer IP (50 mM Tris (pH 7.5)/150 mM NaCl/2 mM $MgCl_2$/0.1% Brij97 (Sigma)/10% glycerol/protease inhibitors) and with PBS-T. After blocking with milk in PBS-T, the membranes were incubated with anti-FKBP52 761 antibody. The presence of FKBP52 was revealed by ECL. Quantitation was performed with Quantity-one software using Chemidoc XRS fitted with a 16 bit CCD camera (Biorad).

Cell Line and Stable DNA Transfection:

Generation of H7C2 cells: The cDNA encoding rabbit FKBP52 was inserted into the HindIII and AccI restriction sites of the pTRE2 vector (Clontech) in order to give pTRE2-FKBP52. Transfection of 100 μg of pTR2-FKBP52 and 10 μg of pTK-hygromicin was carried out in a commercially available PC12 Tet-on cell line (Clontech) that expresses the reverse tetracycline controlled transactivator, using Lipofectamine™ (Invitrogen). Stably transfected cells were selected with 100 μg/ml hygromycin and screened individually.

Cell culture: PC12 cells and H7C2 cells were grown in DMEM containing 10% (v/v) horse serum and 5% (v/v) FBS (Invitrogen) at 37° C. in 90% $O_2$/10% $CO_2$. The differentiated neuronal phenotype of cells grown on plastic dishes coated with 10 μg/ml poly(L)-lysine (Sigma), was induced by adding nerve growth factors (NGF) (Invitrogen) for 5 days. Primary cultures from cerebral cortex of embryonic day 17rat foetuses were carried out. Dissociated cells were plated (50,000 cells per ml) on glass coverslips coated with poly(L-ornithine) and cultured in a defined medium in 95% $O_2$/5% $CO_2$ at 37° C.

Immunocytochemistry: Cells were grown on glass coverslips precoated in 12-well tissue culture plates. Primary cells and PC12 cells were incubated for 2.5 min and 3 min respectively, in PEM buffer (80 mM PIPES, 1 mM $MgCl_2$, 2 mM EGTA, pH6.9) with 0.05% Triton, rinsed with warm Triton-free PEM, fixed for 5 min with methanol at −20° C. and incubated with affinity-purified anti-FKBP52 761 (1/1000), and anti-Tau5 (1/100). Anti-rabbit Alexa Fluor 488-conjugated (Invitrogen), anti-mouse FITC-conjugated or Cy™3 red-conjugated (GE-Healthcare) antibodies were used at 1/500 and 1/1000, respectively. The coverslips were examined by epifluorescence using a Zeiss axioplan 2 microscope with, either a×63 objective or by confocal microscopy (Zeiss, Thornwood, N.Y., USA)

Quantitation of neurite outgrowth: Random field photographs of PC12 and H7C2 cells, in each of three wells, were analyzed with Neuron J software. The average neurite length was determined by measuring the longest neurites of at least 200 cells randomly selected.

Results

Tau FKBP52 association: FKBP52 is widely distributed in the brain as shown by Western blots of cytosolic proteins from several brain areas (FIG. 1). In order To investigate whether MAPs may be involved in the effect of FKBP52 on microtubule stability (9), GST pull-down assays were carried out incubating GST-FKBP52 bound to sepharose beads with microtubules cytosol prepared from adult rat brain. Specifically bound proteins were analyzed by immunoblotting using antibodies directed against MAP1b, MAP2 and Tau. In these experimental conditions, no immunoreactivity was observed for MAP1b or MAP2, but Tau immunoreactivity was present (FIG. 2A). In rat brain homogenates, Tau appears as multiple bands representing different splice isoforms with various degrees of phosphorylation. Several Tau species were also found in pull-down experiments of rat brain cytosol microtubules using GST-FKBP52. Tau immunoreactivity was not detected in controls using purified GST (FIG. 2A). To confirm the specificity of this association, microtubules of adult rat brain cytosol were immunoprecipitated with a polyclonal antibody against FKBP52 Immunoprecipitates were analyzed by Western blotting with a monoclonal Tau antibody. Tau co-immunoprecipitated with FKBP52 but not with a preimmune serum (FIG. 2B). Thus, Tau and FKBP52 form a complex in rat brain. These experiments do not address whether the binding of Tau to FKBP52 is direct or whether it involves additional factors. To investigate this, recombinant Tau (hT40, the longest isoform, expressed in *E. coli* and purified) was spotted onto nitrocellulose and incubated with purified recombinant FKBP52. Then, proteins sequestered by Tau were detected with a polyclonal antibody against FKBP52. As shown on FIG. 2C, FKBP52 was retained in a dose dependent manner by Tau, but not by the GST. These findings indicate a direct interaction between FKBP52 and Tau.

Effect of Tau Phosphorylation on its Interaction with FKBP52: To define whether the phosphorylation of Tau modulates its association with FKBP52, dot blot experiments were performed using recombinant phosphorylated Tau (P-Tau) and hyperphosphorylated Tau (HP-Tau) (18) (FIG. 3A). The specificity of the interaction between FKBP52 and P-Tau or HP-Tau was determined by experiments using as the bait either these phosphorylated ht40, non phosphorylated hT40, or hT40 to which had been added, just prior to spotting, the same amount of cytosol protein as used to obtain phosphorylated or hyperphosphorylated hT40. As shown in FIG. 3B, the amount of FKBP52 recruited by Tau depends on its phosphorylation state. 73% (±7) of FKBP52 was retained by 2.2 μg HP-Tau, whereas only 3.5% and 6.6% were respectively retained by the same amount of hT40 and by hT40 in the presence of cytosolic proteins used as controls. When P-Tau was used as bait, only 41% (±15) of FKBP52 was captured. This difference in binding between HP-Tau and P-Tau to FKBP52 may be explained by the different degree of Tau phosphorylation at specific sites or by the global amount of Tau phosphorylation, or by a combination of both mechanisms (FIG. 3A). In any case, these results underline the importance of Tau phosphorylation for its binding to FKBP52.

Colocalization of Tau and FKBP52 in Primary Cortical Neurons and PC12 Cells.: The subcellular localization of Tau and FKBP52 was examined by immunofluorescence experiments with rat primary cortical neurons. After 6 days of culture, and mild extraction selectively removing unbound cytosolic proteins while retaining proteins associated with the cytoskeleton, double staining was performed on neurons with monoclonal antibody Tau5 and affinity-purified polyclonal anti-FKBP52 antibody. In agreement with an earlier report (19), Tau was concentrated in the distal portion of axons and at the growth cone neck, where a strong accumulation of FKBP52 was also observed (FIG. 4). Colocalization and accumulation of FKBP52 and Tau were also found at the growth cones of PC12 cells (FIG. 4). Very recently it has been reported that Tau is selectively enriched at axonal tips and that this may be due to its specific anchoring (20). Our results suggest that FKBP52 may be involved in the trapping of Tau, and thereby able to influence its subcellular distribution.

FKBP52 Inhibits Tubulin Polymerization Induced by Tau In Vitro.: To demonstrate a functional interaction between Tau and FKBP52, a microtubule kinetic assay was set up. In experiments with purified rat brain tubulin alone, no microtubule was formed, whereas in experiments with recombinant human Tau isoforms, an increased absorbance reflecting microtubule assembly was observed (FIG. 5). However, when Tau was added to the tubulin in the presence of purified recombinant FKBP52, formation of microtubules was prevented, whereas GST was ineffective. Similar results were obtained with the 6 isoforms of human Tau (FIG. 5). We concluded that FKBP52 inhibits the promotion of microtubule assembly by Tau.

FKBP52 Prevents Tau Accumulation and Neurite Outgrowth in PC12 Cells: An FKBP52-inducible expression system based on a tetracycline-responsive element allowing the generation of a stably transformed PC12 cell line was used (21) to determine a cellular role for FKBP52. Among clones which were positively tested, one clone, so called H7C2, was selected and used to study the effects of FKBP52 overexpression on PC12 cells, and to further investigate the possible relationship between FKBP52 and Tau. Under basal conditions H7C2 cells expressed endogenous FKBP52, and treatment with Dox (doxycycline) resulted in a marked increase of recombinant FKBP52 protein expression (FIG. 6A). FKBP52 induction in H7C2 cells was about 4 fold after 5 days of Dox treatment.

The effect of FKBP52 on the accumulation of Tau was examined next. The amount of Tau protein was determined by Western blotting of extracts from cultures of either PC12 cells or H7C2 cells, treated or not with NGF (50 nM) for 5 days with or without Dox. In PC12 cells, FKBP52 expression was unchanged after treatment with NGF (FIG. 6B). As expected, in both PC12 and H7C2 cells an increase in Tau was observed after NGF treatment. However, when H7C2 cells were exposed to Dox in addition to NGF, thus overexpressing FKBP52, no additional accumulation of Tau protein occurred. An increase in Tau protein was still observed in PC12 cells treated with NGF and Dox, ruling out the possibility that Dox was responsible for the lack of decrease in Tau (FIG. 6C). In conclusion, FKBP52 prevented the accumulation of Tau induced by NGF in PC12 cells.

Since one role of Tau is to stimulate neurite outgrowth (12), we investigated the consequence of FKBP52 overexpression on neurite length in both PC12 and H7C2 cells. In the absence of NGF, no neurite outgrowth was observed in H7C2 cells, whether or not they were treated with Dox for a week. However in H7C2 cells treated with 50 nM NGF and Dox, a 40% (±7) decrease in neurite length, compared to control (H7C2 not treated with Dox) was observed (FIG. 6D). The same effect of Dox on neurite length was observed in H7C2 cells treated with 10 or 20 nM NGF. That Dox by itself was involved in the process of neurite outgrowth could be ruled out, since no difference in neurite length between Dox-treated and untreated PC12 cells was observed. The inhibition of neurite outgrowth resulting from FKBP52 overexpression is in agreement with our previous report showing that the loss of FKBP52 in PC12 cells results in the formation of neurite extensions (9). The FKBP52 effect on neurite length could be explained by the binding of Tau to FKBP52, removing Tau from microtubules. In addition the prevention of Tau accumulation by overexpression of FKBP52 is consistent with the decrease of neurite length and evokes a potential role of this immunophilin in Tau function.

Discussion

This newly discovered "anti-Tau" activity of FKBP52 leads us to re-examine the functions of this protein, which was originally identified and cloned as modulator of hormone steroid receptors (8, 22). FKPB52 is a multimodular protein, which includes a peptidyl prolyl isomerase ("rotamase") segment, the function of which is blocked by FK506 (23), rapamycin and some related non-immunosuppressive derivatives. There is a noteworthy structural similarity between FKBP52 and Pin1: both proteins have a peptidyl-prolyl isomerase (PPIase) activity and a specific protein-protein interaction domain (7). Since the Pin1 PPIase activity restores the function of phosphorylated Tau protein in a model of Alzheimer's disease (7), the interaction observed between Tau and FKBP52 may have implications for the pathogenesis of the tauopathies, including Alzheimer's disease. It must be remembered that, unlike FKBP12 (24) FKBP52 does not bind calcineurin (25), and thus FKBP52 does not mediate the immunosuppressant capacity of FK506. Therefore, the pharmacological modulation of the rotamase activity of FKBP52 by non-immunosuppressive FK506/rapamycin derivatives may offer a novel approach for preventing/reducing the pathogenic effects of misfolded Tau.

In addition to its peptidyl prolyl isomerase activity, FKBP52 serves as a molecular chaperone. This activity depends on its tetratricopeptide repeat domain (26) to which the molecular chaperone HSP90 and other proteins bind. It has already been noted that chaperone co-chaperone protein complexes play a critical role in neurodegenerative diseases characterized by Tau accumulation (27). We now report that FKBP52 could decrease the function/accumulation of Tau, and therefore suggest its possible involvement in these described cochaperone systems (27).

Our results establish a role of FKBP52 in Tau function. The interaction described in this report rapidly deserves to be studied further, since effective pharmacological targeting of FKBP52 is likely to become a reality in the near future.

EXAMPLE 2

Effect Of Fkbp52 On Oligomerization Of Tau In Vitro

Aggregates of Tau protein are characteristic of multiple neurodegenerative diseases. (Delacourte A and Bué L, 2000). Studies of conditions for Tau aggregation in vitro have led to different experimental systems including oxidative conditions, inductions by polyanions such as heparin, and by fatty acids such as arachidonic acid (Barghorn S and Mandelkow E, 2002).

To investigate the effect of FKBP52 on Tau oligomerization we monitored by sedimentation assay the ability of recombinant Tau protein (here using the longest isoform) to polymerise in oxidative conditions in presence or absence of recombinant FKBP52. After dialysis of Tau (0.5 mg/ml) overnight at 4° C. in Tris 10 mM pH7.4 and centrifugation at 14000 rpm, quantitative western blotting was used to monitor the polymerization of Tau protein. In this condition sedimentation analysis revealed the presence of Tau in pellet fraction contrary to the experiment carried out in presence of DTT where no detectable pelletable polymers of Tau could be obtained (FIG. 7). This experiment means that Tau in oxidative conditions self polymerise and confirms, as already reported, the importance of cysteines in first step of Tau oligomerization process (Schweers et al 1995).

The effects of coincubating, in oxidative medium, Tau and FKBP52 on Tau oligomerization process were monitored. As shown on FIG. 8 no detectable presence of Tau in pellet fraction could be observed when dialysis were performed in equimolecular presence of FKBP52 where a pelletable polymers of Tau could be observed when coincubation was carried out in presence of GST used as control.

However when sedimentation analysis experiments were realized in varying the concentration of FKBP52 (1 to 0.1 mg/ml) where the concentration of Tau was constant (0.5 mg/ml) the presence of FKBP52 at 0.1 or at 0.25 mg/ml results in increasing Tau polymers in pellet where the presence of equimolecular or two times quantities of FKBP52 versus Tau prevent the presence of pelletable polymers of Tau (FIG. 9). These results suggest a dual role for FKBP52: firstly: a FKBP52 conformational activity on Tau, possibly involving peptidyl prolyl isomerase activity of FKBP52, leading Tau in a favourable proaggregative form; secondly: FKBP52 could protected by possible steric hindrance the ability of Tau to oligomerize via the formation of disulfide bridges.

EXAMPLE 3

Figure 10B:
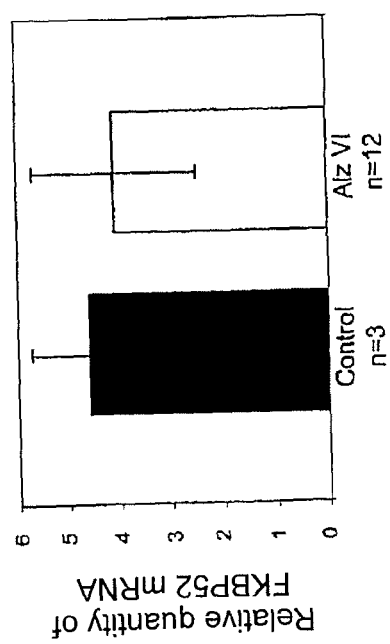

Down Regulation Of Fkbp52 Protein In Brains FROM PATIENTS WITH ALZHEIMER DISEASE Human brain pre frontal cortex, obtained thanks to the access of National BrainBank (GIE NeuroCEB), were homogenized in 5 volumes of buffer containing Tris 10 mM, Saccharose 0.32M, DTT 1 mM and protease inhibitor cocktail. The homogenates were centrifugated at 14000 RPM at 4° C. for 5 min. The supernatant was used as soluble fraction. The pellet was solubilised by homogenization in the same conditions and used as insoluble fraction. FKBP52 levels in the soluble and insoluble fractions were analyzed by western blotting. The FKBP52 level in soluble and insoluble fraction represents respectively 80% and 20% of total FKBP52;

In the aim of elucidate if FKBP52 protein expression level might be altered in patient brain we have compared its expression in the pre frontal cortex of normal control (n=3) and patients with Alzheimer disease (n=12). As shown on FIG. 10 marked reduction of FKBP52 in Alzheimer disease brains is observed in soluble fraction. After normalization with GAPDH (Glyceraldehyde 3-phosphatedehydrogenase) expression levels of FKBP52 found in soluble fraction of Alzheimer disease brains represent 35% (±24) compared to the controls. No modification of expression protein level of FKBP52 could be detectable in insoluble fraction; this last observation suggests that FKBP52 is not trapped in aggregates of Tau.

Subsequently the mRNA expression level of FKBP52 gene was analyzed by real time quantitative RT-PCR (QPCR) in prefrontal cortex of human brain disease and controls. As shown on FIG. 11 no modification of FKBP52 mRNA level is observed in brain diseases versus control. These results indicate that the decreasing of FKBP52 protein expression in the patient brain is due to a post transcriptional mechanism.

REFERENCES

Throughout this application, various references describe the state of the art to which this invention pertains. The disclosures of these references are hereby incorporated by reference into the present disclosure.

Ballatore C, Lee VMY, Trojanowski J Q (2007) Tau-mediated neurodegeneration in Alzheimer's disease and related disorders. *Nat Rev Neurosci* 8: 663-672.

Barghorn S and Mandelkow E. Toward a unified scheme for the aggregation of tau into Alzheimer paired helical filaments. Biochemistry. (2002); 41:14885-96.

Buée L, Bussière T, Buée-Scherrer V, Delacourte A, Hof P R (2000) Tau protein isoforms, phosphorylation and role in neurodegenerative disorders. *Brain Research Review* 33: 95-130.

Chambraud B et al (1993) Overexpression of p59-HBI (FKBP52), full length and domains, and characterization of PPIase activity. *Biochem. Biophys. Res. Commun.* 196: 160-166.

Chambraud B, Belabes H, Fontaine-Lenoir V, Fellous A, Baulieu E E (2007) The immunophilin FKBP52 specifically binds to tubulin and prevents microtubule formation. *FASEB. J* 11: 2787-2797.

Delacourte A and Buée L. Tau pathology: a marker of neurodegenerative disorders. *Curr Opin neurology*, (2000) 13: 371-376.

Delacourte A, Buée L (2000) Tau pathology: a marker of neurodegenerative disorders. *Curr Opin neurology* 13: 371-376.

Dickey C et al (2007) The high-affinity HSP90-CHIP complex recognizes and selectively degrades phosphorylated tau client proteins. *J. Clin; Invest.* 117: 648-658.

Garcia M L, Cleveland D W (2001) Going new places using an old MAP: tau, microtubules and human neurodegenerative disease. *Curr Opin Cell Biol* 13: 41-48.

Goedert M, Jakes R (1990) Expression of separate isoforms of human tau protein:correlation with the tau pattern in brain and effects on tubulin polymerization *EMBO. J.* 9: 4225-4230.

Goedert M, Spillantini M G, Jakes R, Rutherford D, Crowther R A (1989) Multiple isoforms of human microtubule-associated protein-tau: sequences and localization in neurofibrillary tangles of Alzheimer-disease. *Neuron* 3: 519-526.

Goedert M, Wischick C M, Crowther R A, Walker J E, Klug A (1988) Cloning and sequencing of the cDNA encoding a core protein of the paired helical filament of Alzheimer disease: Identification as the microtubule-associated protein tau. *Proc Natl Acad Sci USA* 85: 4051-4055.

Goedert M. et al (1993) The abnormal phosphorylation of tau protein at Ser-202 in Alzheimer disease recapitulates phosphorylation during development. *Proc. Natl. Acad. Sci. U.S.A.* 90: 5066-5070.

Gold B G (1997) FK506 and the Role of Immunophilins in Nerve Regeneration. *Mol Neurobiol* 15: 285-306.

Gossen M, Bujard H (1992) Tight control of gene expression in mammalian cells by tetracycline-responsive promoters. *Proc. Natl. Acad. Sci. U.S.A.* 89: 5547-5551.

Kempf M, Clement A, Faissner A, Lee G, Brandt R (1996) Tau Binds to the Distal Axon Early in Development of Polarity in a Microtubule- and Microfilament-Dependent Manner. *J Neurosci* 16:5583-5592.

Lebeau M C et al (1992) P59, an hsp 90-binding Protein. *J Biol Chem.* 267, 4281-4284.

Lebeau M C, Myagkikh I, Rouvière-Fourmy N, Baulieu E E, Klee C B (1994) Rabbit FKBP-59/HBI does not inhibit calcineurin activity in vitro. *Biochem. Biophys. Res. Com.* 203: 750-755.

Lee V M Y, Goedert M, Trojanowski J Q (2001) Neurodegenerative Tauopathies. *Annu Rev Neurosci* 24: 1121-1159.

Liu J et al (1991). Calcineurin is a common target of cyclophilin-cyclosporin A and FKBP-FK506 complexes. *Cell* 66: 807-815.

Lu K. P, Zhou X. Z. (2007) The prolylisomerase PIN1: a pivotal new twist in phosphorylation signalling and disease. *Nature Rev Mol. Cell. Biol* 8: 904-916.

Mandelkow E M, Mandelkow E (1998) Tau in Alzheimer's disease. *Trends in Cell Biology* 8: 425-427.

Pirkl F, Fischer E, Modrow S, Buchner J (2001) Localization of the Chaperone Domain of FKBP52. *J. Biol. Chem* 276: 37034-37041.

Riggs D L et al (2003) The Hsp90-binding peptidyl isomerise FKBP52 potentiates glucocorticoid signalling in vivo. *EMBO. J.* 22: 1158-1167.

Schiene C, Fischer G (2000) Enzymes that catalyse the restructuring of proteins. *Curr Opin Struct Biol* 10: 40-45.

Schreiber S L (1991) Chemistry and Biology of the Immunophilins and Their Immunosuppressive Ligands. *Science* 251: 283-287.

Schweers O, Mandelkow E-M, Biernat J, and Mandelkow E. Oxidation of cysteine-322 in the repeat domain of microtubule-associated protein tau controls the in vitro assembly of paired helical filaments. Proc Natl Acad Sci. U.S.A. (1995). 92:8463-8467.

Shim S et al (2009) Peptidyl-Prolyl Isomerase FKBP52 Controls Chemotropic Guidance of Neuronal Growth Cones via Regulation of TRPC1 Channel Opening. *Neuron* 64: 471-483.

Snyder S H, Sabatini D M (1995) Immunophilins and the nervous system. *Nat Med* 1: 32-37.

Steiner J P et al (1992) High brain densities of the immunophilin FKBP colocalized with calcineurin. *Nature* 358: 584-587.

Weissmann C et al (2009) Microtubule Binding and Trapping at the Tip of Neurites Regulate Tau Motion in Living Neurons. *Traffic* 11:1655-1668

The invention claimed is:

1. A method of diagnosing and treating a subject thought to have or be predisposed to having a neurological disorder involving Tau dysfunction, which comprises the steps of
   I) obtaining a sample of interest from said subject,
   II) measuring a concentration of the FKBP52 protein in the sample by using an antibody, an antibody derivative or an antibody fragment which binds specifically to the FKBP52 protein, and
   III) administering an effective amount of a compound which modulates a FKBP52 protein level in subjects having or being predisposed to having a neurological disorder involving Tau dysfunction so as to increase the FKBP52 protein level in the subjects.

2. The method of claim 1, wherein the neurological disorder involving Tau dysfunction is Alzheimer's disease.

3. The method according to claim 1 wherein the sample of interest is selected from the group consisting of a cell sample, a biological fluid sample and a biopsy sample obtained from a subject's tissue.

4. The method of claim 3, wherein the biological fluid sample is selected from the group consisting of blood, serum, urine and spinal fluid.

5. The method of claim 3, wherein the cell sample comprises pre frontal cortex cells.

* * * * *